United States Patent
Utsumi et al.

(10) Patent No.: US 8,609,320 B2
(45) Date of Patent: Dec. 17, 2013

(54) RESIST COMPOSITION, METHOD OF FORMING RESIST PATTERN, POLYMERIC COMPOUND AND COMPOUND

(75) Inventors: Yoshiyuki Utsumi, Kawasaki (JP); Takehiro Seshimo, Kawasaki (JP); Tomoyuki Hirano, Kawasaki (JP); Daichi Takaki, Kawasaki (JP); Junichi Tsuchiya, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 13/305,545

(22) Filed: Nov. 28, 2011

(65) Prior Publication Data

US 2012/0135347 A1    May 31, 2012

(30) Foreign Application Priority Data

Nov. 30, 2010    (JP) .................................. 2010-267327

(51) Int. Cl.
G03F 7/04    (2006.01)
G03F 7/00    (2006.01)
C07D 313/20    (2006.01)
C08F 24/00    (2006.01)

(52) U.S. Cl.
USPC ......... 430/270.1; 430/322; 549/268; 526/266

(58) Field of Classification Search
USPC ...................................................... 526/266
See application file for complete search history.

(56) References Cited

U.S. PATENT DOCUMENTS

| 5,945,517 | A | 8/1999 | Nitta et al. |
| 6,949,325 | B2 | 9/2005 | Li et al. |
| 2001/0049073 | A1 | 12/2001 | Hada et al. |
| 2004/0110085 | A1 | 6/2004 | Iwai et al. |
| 2008/0187860 | A1 | 8/2008 | Tsubaki et al. |
| 2010/0062369 | A1 | 3/2010 | Dazai et al. |

FOREIGN PATENT DOCUMENTS

| JP | H09-208554 | 8/1997 |
| JP | 11-035551 | 2/1999 |
| JP | 11-035552 | 2/1999 |
| JP | 11-035573 | 2/1999 |
| JP | 2000-206694 | 7/2000 |
| JP | 2003-241385 | 8/2003 |
| JP | 2005-336452 | 12/2005 |
| JP | 2006-259582 | 9/2006 |
| JP | 2006-317803 | 11/2006 |
| JP | 2008-292975 | 12/2008 |
| JP | 2010-134417 | 6/2010 |
| WO | WO 2004/074242 A2 | 9/2004 |

OTHER PUBLICATIONS

Takeda, et al. "Allyl Isopropenyl Dicarbonate; A Convenient Reagent for the Preparation of Allyl Esters of Carboxylic Acids" Jan. 2, 1995. Tetrahedron Letters, vol. 36, No. 1, pp. 113-114.*

* cited by examiner

*Primary Examiner* — Cynthia H Kelly
*Assistant Examiner* — Alyssa L Cepluch
(74) *Attorney, Agent, or Firm* — Knobbe Martens Olson & Bear LLP

(57) ABSTRACT

A resist composition, a method of forming a resist pattern using the resist composition, a novel polymeric compound and a compound useful as a monomer for the polymeric compound,
the resist composition including a base component (A) that exhibits changed solubility in a developing solution under action of acid and an acid generator component (B) that generates acid upon exposure,
the base component (A) containing a resin component (A0) including a structural unit (a0) represented by general formula (a0) shown below

[Chemical Formula 1]

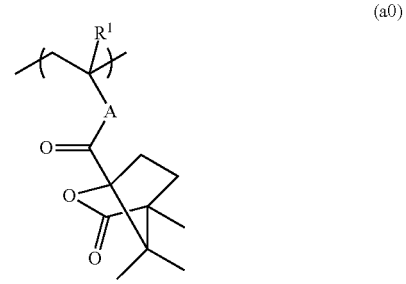

(a0)

in which A represents a divalent linking group; and $R^1$ represents a hydrogen atom or a hydrocarbon group of 1 to 6 carbon atoms which may have a substituent.

14 Claims, No Drawings

RESIST COMPOSITION, METHOD OF FORMING RESIST PATTERN, POLYMERIC COMPOUND AND COMPOUND

BACKGROUND OF THE INVENTION

1. Field of the Invention

The present invention relates to a resist composition, a method of forming a resist pattern using the resist composition, a novel polymeric compound and a compound useful as a monomer for the polymeric compound.

Priority is claimed on Japanese Patent Application No. 2010-267327, filed Nov. 30, 2010, the content of which is incorporated herein by reference.

2. Description of Related Art

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength (and increasing the energy) of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use an exposure light source having a shorter wavelength (and a higher energy level) than these excimer lasers, such as an electron beam, extreme ultraviolet radiation (EUV), and X-ray.

Resist materials for use with these types of exposure light sources require lithography properties such as a high resolution capable of reproducing patterns of minute dimensions, and a high level of sensitivity to these types of exposure light sources.

As a resist material which satisfies these conditions, a chemically amplified resist composition is used, which includes a base component that exhibits a changed solubility in a developing solution under the action of acid and an acid generator component that generates acid upon exposure.

For example, when the above developing solution is an alkali developing solution (when the process is an alkali developing process), a chemically amplified positive resist composition typically contains a resin component (base resin) that exhibits increased solubility in an alkali developing solution under the action of acid, and an acid generator component. If the resist film formed using this resist composition is selectively exposed during formation of a resist pattern, then acid is generated from the acid generator component within the exposed portions, and the action of this acid causes an increase in the solubility of the resin component in an alkali developing solution, making the exposed portions soluble in the alkali developing solution. On the other hand, the unexposed portions remain. As a result, a positive pattern is formed. Here, a resin that exhibits increased polarity by the action of acid has been used as the base resin, and the solubility in an alkali developing solution increases while the solubility in an organic solvent reduces. For this reason, if a process (hereafter, sometimes referred to as a "solvent developing process" or "negative developing process") using a developing solution containing an organic solvent (organic developing solution) is employed instead of the alkali developing process, the solubility in an organic developing solution is relatively reduced within the exposed portions. As a result, in this solvent developing process, the unexposed portions of the resist film are dissolved and removed by the organic developing solution whereas the exposed portions remain as a pattern, and hence, a negative resist pattern can be formed. For example, a negative developing process has been proposed in Patent Document 1.

Examples of these acid generators usable in a chemically amplified resist composition are numerous, and include onium salt-based acid generators, oxime sulfonate-based acid generators, diazomethane-based acid generators, nitrobenzylsulfonate-based acid generators, iminosulfonate-based acid generators, and disulfone-based acid generators. Of these, as an onium salt-based acid generator, iodonium salts containing iodonium ions as cations and sulfonium salts containing sulfonium ions as cations have conventionally been used.

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm. Examples of such resins include a resin containing a structural unit having an acid dissociable, dissolution inhibiting group that is dissociated by the action of acid generated from the acid generator, as well as a structural unit having a lactone structure (for example, refer to Patent Document 2). Structural units having a lactone structure are generally considered as being effective in improving the adhesion between the resist film and the substrate, and increasing the compatibility with an alkali developing solution, thereby contributing to improvement in various lithography properties.

Further, in recent years, resins containing, instead of or in addition to a structural unit having a lactone structure, a structural unit having a cyclic group that includes a —$SO_2$— moiety within the ring skeleton have also been used (for example, refer to Patent Document 3). Further, structural units having a cyclic group that includes a —$SO_2$— moiety within the ring skeleton are generally considered as being effective in improving the adhesion between the resist film and the substrate, and increasing the distribution homogeneity of acid generator within the resist film, thereby contributing to improvement in various lithography properties.

DOCUMENTS OF RELATED ART

Patent Documents

[Patent Document 1] Japanese Unexamined Patent Application, First Publication No. 2008-292975

[Patent Document 2] Japanese Unexamined Patent Application, First Publication No. 2003-241385

[Patent Document 3] Japanese Unexamined Patent Application, First Publication No. 2010-134417

SUMMARY OF THE INVENTION

In the future, as further progress is made in lithography techniques and in the miniaturization of resist patterns, further improvement in various lithography properties has been demanded with respect to the resist materials. Examples of the lithography properties that require further improvements include line width roughness (LWR) and resolution.

However, in those cases where a conventional base resin as described in Patent Document 3 has been used, there was still room for improvement in terms of the lithography properties of the obtained resist pattern.

The present invention takes the above circumstances into consideration, with an object of providing a resist composition, a method of forming a resist pattern using the resist composition, a novel polymeric compound and a compound useful as a monomer for the polymeric compound.

For solving the above-mentioned problems, the present invention employs the following aspects.

That is, a first aspect of the present invention is a resist composition including a base component (A) that exhibits changed solubility in a developing solution under the action of acid and an acid generator component (B) that generates acid upon exposure, the resist composition characterized in that the base component (A) contains a resin component (A0) including a structural unit (a0) represented by general formula (a0) shown below.

[Chemical Formula 1]

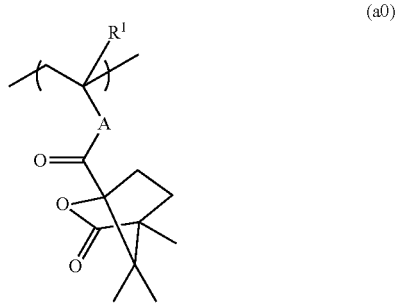

(a0)

In the formula, A represents a divalent linking group; and $R^1$ represents a hydrogen atom or a hydrocarbon group of 1 to 6 carbon atoms which may have a substituent.

A second aspect of the present invention is a method of forming a resist pattern, including: applying a resist composition of the first aspect to a substrate to form a resist film on the substrate; conducting exposure of the resist film; and developing the resist film to form a resist pattern.

A third aspect of the present invention is a polymeric compound including a structural unit (a0) represented by general formula (a0) shown below.

[Chemical Formula 2]

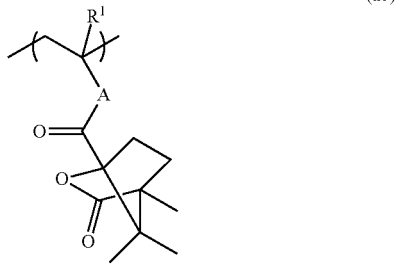

(a0)

In the formula, A represents a divalent linking group; and $R^1$ represents a hydrogen atom or a hydrocarbon group of 1 to 6 carbon atoms which may have a substituent.

A fourth aspect of the present invention is a compound represented by general formula (I) shown below.

[Chemical Formula 3]

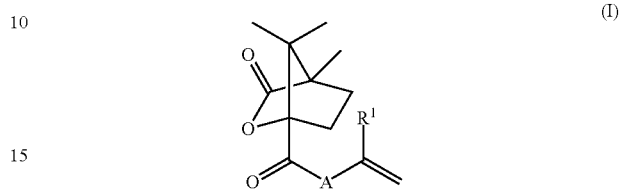

(I)

In the formula, A represents a divalent linking group; and $R^1$ represents a hydrogen atom or a hydrocarbon group of 1 to 6 carbon atoms which may have a substituent.

In the present description and claims, the term "aliphatic" is a relative concept used in relation to the term "aromatic", and defines a group or compound or the like that has no aromaticity.

The term "alkyl group" includes linear, branched or cyclic, monovalent saturated hydrocarbon, unless otherwise specified.

The term "alkylene group" includes linear, branched or cyclic divalent saturated hydrocarbon, unless otherwise specified. The same applies for the alkyl group within an alkoxy group.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with fluorine atoms.

The term "structural unit" refers to a monomer unit that contributes to the formation of a polymeric compound (namely, a resin, polymer or copolymer).

An "acrylate ester" is a compound in which the hydrogen atom at the carboxyl group terminal of acrylic acid ($CH_2$=CH—COOH) has been substituted with an organic group.

A "structural unit derived from an acrylate ester" refers to a structural unit that is formed by the cleavage of the ethylenic double bond of an acrylate ester.

With respect to an "acrylate ester in which a hydrogen atom bonded to the carbon atom on the α-position may be substituted with a substituent", examples of the substituent include a halogen atom, an alkyl group of 1 to 5 carbon atoms, a halogenated alkyl group of 1 to 5 carbon atoms and a hydroxyalkyl group.

With respect to the "structural unit derived from an acrylate ester", the "α-position (the carbon atom on the α-position)" refers to the carbon atom having the carbonyl group bonded thereto, unless specified otherwise.

Examples of halogen atom for the substituent include a fluorine atom, a chlorine atom, a bromine atom and an iodine atom. Specific examples of the alkyl group of 1 to 5 carbon atoms for the substituent include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group of 1 to 5 carbon atoms for the substituent include groups in which some or all of the hydrogen atoms of the aforementioned "alkyl group of 1 to 5 carbon atoms for the substituent" are substituted with halogen atoms. Examples of the halogen atom include a fluorine atom, a chlorine atom, a bromine atom and an iodine atom, and a fluorine atom is particularly desirable. Specific examples of the hydroxyalkyl group for the substituent include groups in which some or all of the hydrogen atoms of the aforementioned "alkyl group of 1 to 5 carbon atoms for the substituent" are substituted with hydroxy groups.

In the present invention, it is preferable that a hydrogen atom, an alkyl group of 1 to 5 carbon atoms or a halogenated alkyl group of 1 to 5 carbon atoms, and more preferably a hydrogen atom, an alkyl group of 1 to 5 carbon atoms or a fluorinated alkyl group of 1 to 5 carbon atoms, is bonded to the carbon atom on the α-position. In terms of industrial availability, a hydrogen atom or a methyl group is the most desirable.

The term "hydroxystyrene derivative" is a generic term that includes both the narrow definition of hydroxystyrene, as well as compounds in which the α-position hydrogen atom of the narrowly defined hydroxystyrene has been substituted with a substituent group such as an alkyl group or a halogenated alkyl group or the like, and derivatives thereof. Furthermore, unless stated otherwise, a carbon atom on the α-position of hydroxystyrene refers to the carbon atom to which the benzene ring is bonded.

The expression "structural unit derived from a hydroxystyrene derivative" describes a structural unit that is formed by the cleavage of the ethylenic double bond of the hydroxystyrene derivative.

The term "styrene" refers to a general concept including styrene itself, as well as structures in which the hydrogen atom at the α-position in styrene has been substituted by another substituent group such as an alkyl group.

The term "structural unit derived from styrene" refers to a structural unit which is formed by the cleavage of the ethylenic double bond of styrene. In the styrene, the hydrogen atom of the phenyl group may be substituted with a substituent such as an alkyl group of 1 to 5 carbon atoms.

The term "exposure" is used as a general concept that includes irradiation with any form of radiation.

According to the present invention, there are provided a resist composition that exhibits excellent lithography properties, a method of forming a resist pattern using the resist composition, a novel polymeric compound and a compound useful as a monomer for the polymeric compound.

DETAILED DESCRIPTION OF THE INVENTION

<<Resist Composition>>

The resist composition according to the first aspect of the present invention includes a base component (A) (hereafter, referred to as "component (A)") that exhibits changed solubility in a developing solution under the action of acid and an acid generator component (B) (hereafter, referred to as "component (B)") that generates acid upon exposure.

With respect to a resist film formed using the resist composition, when a selective exposure is conducted during formation of a resist pattern, acid is generated from the component (B), and the generated acid acts on the component (A) to change the solubility of the component (A) in a developing solution. As a result, the solubility of the exposed portions of this resist film in a developing solution is changed, whereas the solubility of the unexposed portions in a developing solution remains unchanged. Therefore, the exposed portions are dissolved and removed by developing in the case of a positive pattern, whereas the unexposed portions are dissolved and removed in the case of a negative pattern, and hence, a resist pattern can be formed.

The resist composition of the present invention may be either a negative resist composition or a positive resist composition.

In the present description, a resist composition for forming a positive pattern in which the exposed portions are dissolved and removed will be referred to as a positive resist composition, and a resist composition for forming a negative pattern in which the unexposed portions are dissolved and removed will be referred to as a negative resist composition.

<Component (A)>

The component (A) in the present invention is a base component that contains a resin component (A0) (hereafter, referred to as "component (A0)") including a structural unit (a0) represented by the above general formula (a0). The structural unit (a0) will be described later.

In the present invention, the term "base component" refers to an organic compound capable of forming a film, and preferably refers to an organic compound having a molecular weight of 500 or more. When the organic compound has a molecular weight of 500 or more, the film-forming ability is improved, and a resist pattern of nano level can be easily formed.

The "organic compounds having a molecular weight of 500 or more" which can be used as the base component can be broadly classified into non-polymers and polymers.

In general, as a non-polymer, any of those which have a molecular weight in the range of 500 to less than 4,000 is used. Hereafter, a non-polymer having a molecular weight in the range of 500 to less than 4,000 is referred to as a "low molecular weight compound".

As a polymer, any of those which have a molecular weight of 1,000 or more is generally used. Hereafter, a polymer having a molecular weight of 1,000 or more is referred to as a "polymeric compound". With respect to a polymeric compound, the "molecular weight" is the weight average molecular weight in terms of the polystyrene equivalent value determined by gel permeation chromatography (GPC). Hereafter, a polymeric compound is frequently referred to simply as a "resin".

[Component (A0)]

When the resist composition of the present invention is a "negative resist composition for alkali developing process" for forming a negative pattern in the alkali developing process, as the component (A0), a resin component that is soluble in an alkali developing solution is used, and a cross-linker component is further blended thereto.

In the negative resist composition for alkali developing process, when acid is generated from the component (B) upon exposure, the action of this acid causes cross-linking between the base component and the cross-linker component, and the cross-linked portion becomes hardly soluble in an alkali developing solution. As a result, during resist pattern formation, when a resist film obtained by applying the negative resist composition to a substrate is selectively exposed, the exposed portions become hardly soluble in an alkali developing solution, whereas the unexposed portions remain soluble in the alkali developing solution, and hence, a resist pattern can be formed by alkali developing.

In general, as the component (A0) of the negative resist composition for alkali developing process, a resin that is soluble in an alkali developing solution (hereafter, referred to as "alkali-soluble resin") is used.

As an alkali-soluble resin, it is preferable to use, for example, a resin having a structural unit derived from at least one of α-(hydroxyalkyl)acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; an acrylic resin or polycycloolefin resin having a sulfoneamide group, and in which a hydrogen atom bonded to the carbon atom on the α-position may be substituted with a substituent, as disclosed in U.S. Pat. No. 6,949,325; an acrylic resin having a fluorinated alcohol, and in which a hydrogen atom bonded to the carbon atom on the α-position may be substituted with a substituent, as disclosed in U.S. Pat. No. 6,949,325, Japanese Unexamined Patent Application, First Publication No. 2005-336452 or Japanese Unexamined Patent Application, First Publication No. 2006-317803; and a polycycloolefin resin having a fluorinated alcohol, as disclosed in Japanese Unexamined Patent Application, First Publication No. 2006-259582, as such resins enable the formation of a favorable resist pattern with minimal swelling.

Here, the term "α-(hydroxyalkyl)acrylic acid" refers to, among the acrylic resins in which a hydrogen atom bonded to the carbon atom on the α-position may be substituted with a substituent, one or both of acrylic acid, in which a hydrogen atom is bonded to the carbon atom on the α-position having the carboxyl group bonded thereto, and α-hydroxyalkylacrylic acid, in which a hydroxyalkyl group (and preferably a hydroxyalkyl group of 1 to 5 carbon atoms) is bonded to the carbon atom on the α-position.

As the cross-linker component, typically, an amino-based cross-linker, such as a glycoluril having a methylol group or alkoxymethyl group, or a melamine-based cross-linker is preferable, as it enables formation of a favorable resist pattern with minimal swelling. The amount of the cross-linker component added is preferably within the range from 1 to 50 parts by weight, relative to 100 parts by weight of the alkali-soluble resin.

When the resist composition of the present invention is a resist composition for forming a positive pattern in the alkali developing process and forming a negative pattern in the solvent developing process, as the component (A0), a resin component (A1) (hereafter, referred to as "component (A1)") that exhibits increased polarity by the action of acid is preferably used. Because the polarity of the resin component changes before and after the exposure due to the use of the component (A1), an excellent development contrast can be achieved, not only in the alkali developing process, but also in the solvent developing process.

In those cases where the alkali developing process is employed, the component (A1) is substantially insoluble in an alkali developing solution prior to exposure, but when acid is generated from the component (B) upon exposure, the action of this acid causes an increase in the polarity, thereby increasing the solubility of the component (A1) in the alkali developing solution. Accordingly, during resist pattern formation, when a resist film formed by applying the resist composition onto a substrate is selectively exposed, the exposed portions change from being hardly soluble in an alkali developing solution to being alkali-soluble, whereas the unexposed portions remain alkali-insoluble, meaning a positive pattern can be formed by alkali developing.

Further, in those cases where the solvent developing process is employed, the component (A1) is highly soluble in an organic developing solution prior to exposure, but when acid is generated from the component (B) upon exposure, the action of this acid causes an increase in the polarity, thereby reducing the solubility of the component (A1) in the organic developing solution. Accordingly, during resist pattern formation, when a resist film formed by applying the resist composition onto a substrate is selectively exposed, the exposed portions change from being soluble in an organic developing solution to being hardly soluble, whereas the unexposed portions remain soluble. As a result, by developing using an organic developing solution, a contrast can be generated between the exposed portions and the unexposed portions, and hence, a negative pattern can be formed.

In the resist composition of the present invention, the component (A0) is preferably a resin component (namely, the component (A1)) that exhibits increased polarity by the action of acid. That is, the resist composition of the present invention is preferably a chemically amplified resist composition that becomes a positive resist composition in the alkali developing process and becomes a negative resist composition in the solvent developing process.

[Component (A1)]

In the present invention, the structural unit (a0) represented by the above formula (a0) is preferably included in the component (A1).

Further, the component (A1) preferably includes a structural unit (a1) containing an acid decomposable group that exhibits increased polarity by the action of acid.

It is preferable that the component (A1) further include at least one type of structural unit (a2) selected from the group consisting of structural units containing a —$SO_2$— containing cyclic group and derived from an acrylate ester in which a hydrogen atom bonded to the carbon atom on the α-position may be substituted with a substituent, and structural units containing a lactone-containing cyclic group and derived from an acrylate ester in which a hydrogen atom bonded to the carbon atom on the α-position may be substituted with a substituent.

Further, it is preferable that the component (A1) also include a structural unit (a3) containing a polar group-containing aliphatic hydrocarbon group and derived from an acrylate ester in which a hydrogen atom bonded to the carbon atom on the α-position may be substituted with a substituent.

(Structural Unit (a0))

The structural unit (a0) is a structural unit represented by general formula (a0) shown below.

[Chemical Formula 4]

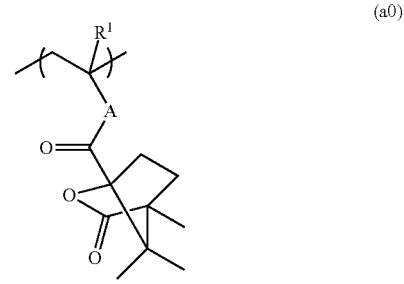

(a0)

In the formula, A represents a divalent linking group; and $R^1$ represents a hydrogen atom or a hydrocarbon group of 1 to 6 carbon atoms which may have a substituent.

In formula (a0), $R^1$ represents a hydrogen atom or a hydrocarbon group of 1 to 6 carbon atoms which may have a substituent.

The alkyl group of 1 to 6 carbon atoms for $R^1$ is preferably a linear or branched alkyl group, and specific examples thereof include a methyl group, an ethyl group, a propyl group, an isopropyl group, an n-butyl group, an isobutyl group, a tert-butyl group, a pentyl group, an isopentyl group, a neopentyl group, a heptyl group and an n-heptyl group.

The alkyl group of 1 to 6 carbon atoms for $R^1$ may have a substituent. The substituent is preferably a halogen atom. Examples of the halogen atom include a fluorine atom, a chlorine atom, a bromine atom and an iodine atom, and a fluorine atom is particularly desirable.

In formula (a0), A represents a divalent linking group.

Preferred examples of the divalent linking group for A include divalent hydrocarbon groups which may have a substituent, and divalent linking groups containing a hetero atom.

The description that the hydrocarbon group "may have a substituent" means that some or all of the hydrogen atoms within the hydrocarbon group may be substituted with an atom other than a hydrogen atom or with a group.

The hydrocarbon group may be either an aliphatic hydrocarbon group or an aromatic hydrocarbon group. An "aliphatic hydrocarbon group" refers to a hydrocarbon group that has no aromaticity.

The aliphatic hydrocarbon group may be saturated or unsaturated. In general, the aliphatic hydrocarbon group is preferably saturated.

Specific examples of the aliphatic hydrocarbon group for A include linear and branched aliphatic hydrocarbon groups, and aliphatic hydrocarbon groups containing a ring in the structure thereof.

The linear or branched aliphatic hydrocarbon group is preferably a group of 1 to 10 carbon atoms, more preferably 1 to 8 carbon atoms, still more preferably 1 to 5 carbon atoms, and most preferably 1 or 2 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; alkyltrimethylene groups such as —CH($CH_3$)$CH_2CH_2$—, and —$CH_2CH(CH_3$)$CH_2$—; and alkyltetramethylene groups such as —CH($CH_3$)$CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated alkyl group of 1 to 5 carbon atoms, and an oxygen atom (=O).

Examples of the aliphatic hydrocarbon group containing a ring in the structure thereof include cyclic aliphatic hydrocarbon groups (groups in which two hydrogen atoms have been removed from an aliphatic hydrocarbon ring), and groups in which this type of cyclic aliphatic hydrocarbon group is either bonded to the terminal of an aforementioned chain-like aliphatic hydrocarbon group, or interposed within the chain of an aforementioned chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

The aromatic hydrocarbon group for A preferably has 5 to 30 carbon atoms, more preferably 6 to 20 carbon atoms, and still more preferably 6 to 15 carbon atoms. Examples of the aromatic hydrocarbon groups include a divalent aromatic hydrocarbon group in which one hydrogen atom has been further removed from a benzene ring of a monovalent aromatic hydrocarbon group such as a phenyl group, a biphenyl group, a fluorenyl group, a naphthyl group, an anthryl group or a phenanthryl group; an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been further removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

With respect to the "divalent linking group containing a hetero atom" for A, the hetero atom refers to an atom other than carbon and hydrogen, and examples thereof include an oxygen atom, a nitrogen atom, a sulfur atom and a halogen atom.

Specific examples of the divalent linking group containing a hetero atom include —O—, —C(=O)—, —C(=O)—O—, a carbonate bond (—O—C(=O)—O—), —NH— (H may be replaced with a substituent such as an alkyl group, an acyl group or the like), —NH—C(=O)—, =N—, —S—, —S(=O)$_2$—, and —S(=O)$_2$—O—. Further, a combination of any one of these "divalent linking groups containing a hetero atom" with a divalent hydrocarbon group can also be used. As examples of the divalent hydrocarbon group, the same groups as those described above for the hydrocarbon group which may have a substituent can be given, and a linear or branched aliphatic hydrocarbon group or an aliphatic hydrocarbon group containing a ring in the structure thereof is preferable.

A may or may not have an acid dissociable portion in the structure thereof.

An "acid dissociable portion" refers to a portion within the organic group which is dissociated from the organic group by the action of acid generated upon exposure. When A has an acid dissociable portion, it preferably has an acid dissociable portion having a tertiary carbon atom.

In the present invention, A is preferably a divalent linking group containing a hetero atom. Examples of particularly preferred linking groups include groups represented by formulas: —C(=O)—$X^0$-$A^0$-$X^0$—, —C(=O)—$X^0$—$B^0$—$X^0$—, —$B^0$—C(=O)—$X^0$-$A^0$-$X^0$— and —C(=O)—$X^0$-$A^0$-$X^0$-$A^0$-$X^0$— [in the formulas, each $X^0$ independently represents O, $NR^{04}$ ($R^{04}$ represents a hydrogen atom or a hydrocarbon group which may have a substituent), S or $SO_2$—O—, each $A^0$ independently represents an aliphatic hydrocarbon group which may have a substituent, each $B^0$ independently represents an aromatic hydrocarbon group, wherein a plurality of $X^0$ or $A^0$ may be the same or different, respectively].

As examples of the aliphatic hydrocarbon group which may have as a substituent for $A^0$, the same aliphatic hydrocarbon groups as those described above for A with respect to the "divalent hydrocarbon group which may have a substituent" can be given. Of these, linear alkylene groups, groups in which two hydrogen atoms have been removed from the aliphatic hydrocarbon rings, or combinations thereof are preferred. The aliphatic hydrocarbon ring may be either monocyclic or polycyclic.

As examples of the aromatic hydrocarbon group which may have as a substituent for $B^0$, the same aromatic hydrocarbon groups as those described above for A with respect to the "divalent hydrocarbon group which may have a substituent" can be given.

Of these, A is preferably a group represented by formula —C(=O)—$X^0$-$A^0$-$X^0$— or —$B^0$—$X^0$—, more preferably a group represented by formula —C(=O)—$X^0$—$(CH_2)_{n01}$—$X^0$— (n01 is an integer of 2 or more, and preferably an integer of 2 to 10) or —$B^0$—$X^0$—, and particularly preferably a group represented by formula —C(=O)—O—$(CH_2)_{n01}$—O— or —$B^0$—O—.

Specific examples of monomers for deriving the structural unit (a0) are shown below. In the following formulas, $R^1$, $X^0$ and n01 are the same as defined above; 101 represents an integer of 1 or more, preferably an integer of 1 to 5; m01 represents an integer of 0 or more, preferably an integer of 0 to 5.

[Chemical Formula 5]

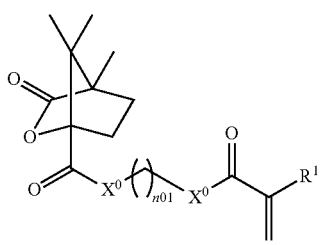

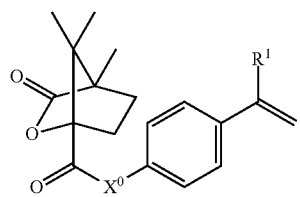

-continued

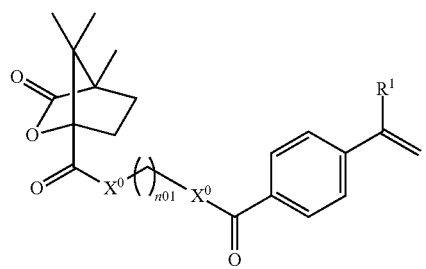

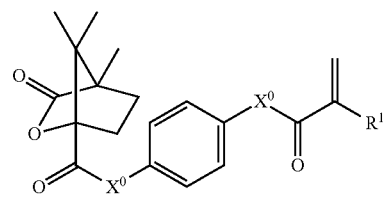

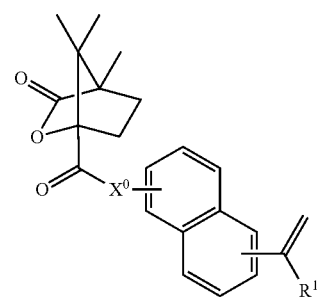

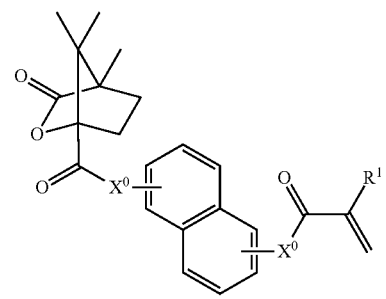

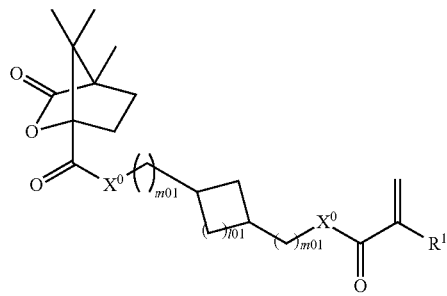

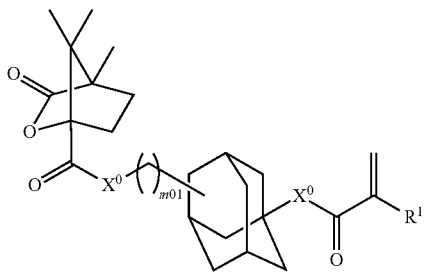

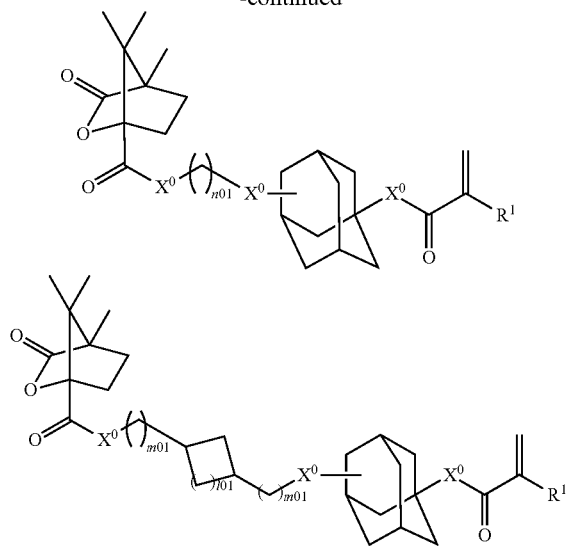

As the structural unit (a0), one type of structural unit may be used alone, or two or more types of structural units may be used in combination.

In terms of achieving excellent line width roughness (LWR), resolution and the like in the formation of a resist pattern using a positive resist composition containing the component (A1), the amount of the structural unit (a0) within the component (A1), based on the combined total of all structural units constituting the component (A1) is preferably 1 to 70 mol %, more preferably 5 to 70 mol %, and most preferably 10 to 65 mol %.

(Structural Unit (a1))

The structural unit (a1) is a structural unit containing an acid decomposable group that exhibits increased polarity by the action of acid. The structural unit (a1) is preferably a structural unit (a11) derived from an acrylate ester, in which a hydrogen atom bonded to the carbon atom on the α-position may be substituted with a substituent, and also containing an acid decomposable group that exhibits increased polarity by the action of acid; or a structural unit (a12) derived from a hydroxystyrene derivative and also containing an acid decomposable group that exhibits increased polarity by the action of acid. The component (A1) may contain both of the structural units (a11) and (a12) or may contain either one of them.

(Structural Unit (a11))

The structural unit (a11) is a structural unit derived from an acrylate ester, in which a hydrogen atom bonded to the carbon atom on the α-position may be substituted with a substituent, and is also a structural unit containing an acid decomposable group that exhibits increased polarity by the action of acid.

The term "acid decomposable group" refers to a group exhibiting acid decomposability in which at least a part of the bond within the structure of this acid decomposable group may be cleaved by the action of acid generated from the component (B) upon exposure.

Examples of acid decomposable groups that exhibit increased polarity by the action of an acid include groups which are decomposed by the action of acid to form a polar group.

Examples of the polar group include a carboxyl group, a hydroxyl group, an amino group and a sulfo group (—$SO_3H$). Of these, polar groups containing an —OH moiety within the structure (hereafter, sometimes referred to as an "OH-containing polar group") are preferable, a carboxyl group or a hydroxyl group is more preferable, and a carboxyl group is particularly desirable.

Specific examples of acid decomposable groups include groups in which the aforementioned polar group is protected with an acid dissociable group (such as groups in which the hydrogen atom of an OH-containing polar group is protected with an acid dissociable group).

An "acid dissociable group" is a group exhibiting acid dissociability in which at least the bond between the acid dissociable group and the atom adjacent to this acid dissociable group may be cleaved by the action of acid generated from the component (B) upon exposure. The acid dissociable group constituting an acid decomposable group needs to be a group that exhibits lower polarity than the polar group formed by the dissociation of this acid dissociable group. Due to this, when the acid dissociable group dissociates by the action of acid, a polar group that exhibits higher polarity than this acid dissociable group is formed, thereby increasing the polarity. As a result, the polarity of the entire component (A1) increases. Due to the increase in polarity, in those cases where the alkali developing process is employed, the solubility in an alkali developing solution relatively increases. On the other hand, in those cases where the solvent developing process is employed, the solubility in an organic developing solution containing an organic solvent reduces.

As the acid dissociable group in the structural unit (a11), any of the groups that have been proposed as acid dissociable groups for the base resins of chemically amplified resists can be used. Generally, groups that form either a cyclic or chain-like tertiary alkyl ester with the carboxyl group of the (meth)acrylic acid, and acetal-type acid dissociable groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom to form a carboxyl group, thereby increasing the polarity of the component (A1).

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable groups".

Examples of tertiary alkyl ester-type acid dissociable groups include aliphatic branched, acid dissociable groups and aliphatic cyclic group-containing acid dissociable groups.

Here, the term "aliphatic branched" in the present description and claims refers to a branched structure having no aromaticity.

The "aliphatic branched, acid dissociable group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable groups include tertiary alkyl groups of 4 to 8 carbon atoms, and specific examples include a tert-butyl group, a tert-pentyl group and a tert-heptyl group.

The term "aliphatic cyclic group" refers to a monocyclic group or polycyclic group that has no aromaticity.

The "aliphatic cyclic group" within the structural unit (a11) may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group. The base ring of this aliphatic cyclic group, excluding the substituents, preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms.

As the aliphatic cyclic groups, for example, groups in which one or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable group, for example, a group which has a tertiary carbon atom on the ring structure of the cyclic alkyl group can be mentioned. Specific examples include a 2-methyl-2-adamantyl group and a 2-ethyl-2-adamantyl group, like the groups represented by general formulas (1-1) to (1-9) shown below.

Further, examples of the aliphatic branched, acid dissociable groups include, like the groups represented by general formulas (2-1) to (2-6) shown below, groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto.

[Chemical Formula 6]

(1-1)

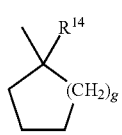

(1-2)

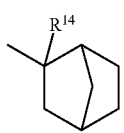

(1-3)

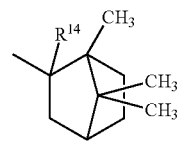

(1-4)

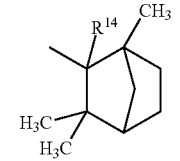

(1-5)

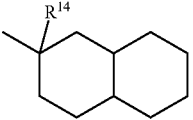

(1-6)

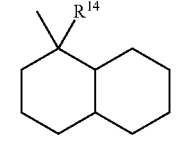

(1-7)

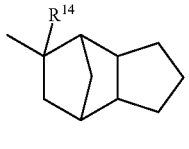

(1-8)

(1-9)

In the formulas above, $R^{14}$ represents an alkyl group; and g represents an integer of 0 to 8.

[Chemical Formula 7]

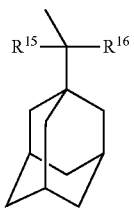

(2-1)

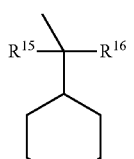

(2-2)

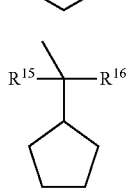

(2-3)

(2-4)

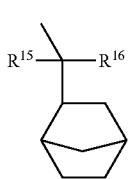

(2-5)

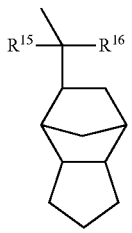

(2-6)

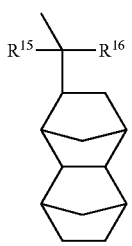

In the formulas above, each of $R^{15}$ and $R^{16}$ independently represents an alkyl group (which may be linear or branched, and preferably has 1 to 5 carbon atoms).

As the alkyl group for $R^{14}$, a linear or branched alkyl group is preferable.

The linear alkyl group preferably has 1 to 5 carbon atoms, more preferably 1 to 4 carbon atoms, and still more preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5 carbon atoms. Specific examples of such branched alkyl groups include an isopropyl group, an isobutyl group, a tert-butyl group, an isopentyl group and a neopentyl group, and an isopropyl group is particularly desirable.

g is preferably an integer of 0 to 3, more preferably an integer of 1 to 3, and still more preferably 1 or 2.

As the alkyl group for $R^{15}$ and $R^{16}$, the same alkyl groups as those for $R^{14}$ can be used.

In formulas (1-1) to (1-9) and (2-1) to (2-6), part of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of the substituent include an alkyl group of 1 to 5 carbon atoms, a fluorine atom and a fluorinated alkyl group of 1 to 5 carbon atoms.

An "acetal-type acid dissociable group" generally substitutes a hydrogen atom at the terminal of an OH-containing polar group such as a carboxyl group or hydroxyl group, so as to be bonded with an oxygen atom. When acid is generated upon exposure, the generated acid acts to break the bond between the acetal-type acid dissociable group and the oxygen atom to which the acetal-type, acid dissociable group is bonded, thereby forming an OH-containing polar group such as a carboxyl group or a hydroxyl group. As a result, the polarity of the component (A1) increases.

Examples of acetal-type acid dissociable groups include groups represented by general formula (p1) shown below.

[Chemical Formula 8]

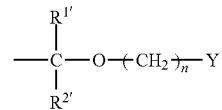

(p1)

In the formula, each of $R^{1'}$ and $R^{2'}$ independently represents a hydrogen atom or an alkyl group of 1 to 5 carbon atoms; n represents an integer of 0 to 3; and Y represents an alkyl group of 1 to 5 carbon atoms or an aliphatic cyclic group.

In general formula (p1) above, n is preferably an integer of 0 to 2, more preferably 0 or 1, and most preferably 0.

As the alkyl group of 1 to 5 carbon atoms for $R^{1'}$ and $R^{2'}$, the same alkyl groups of 1 to 5 carbon atoms as those described above for R can be used, and a methyl group or an ethyl group is preferable, and a methyl group is most preferable.

In the present invention, it is preferable that at least one of $R^{1'}$ and $R^{2'}$ be a hydrogen atom. That is, it is preferable that the acid dissociable group (p1) is a group represented by general formula (p1-1) shown below.

[Chemical Formula 9]

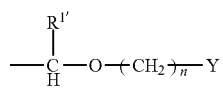

(p1-1)

In the formula, $R^{1'}$, n and Y are the same as defined above.

As the alkyl group of 1 to 5 carbon atoms for Y, the same alkyl groups of 1 to 5 carbon atoms as those described above for R can be used.

As the aliphatic cyclic group for Y, any of the aliphatic monocyclic or polycyclic groups that have been proposed for conventional ArF resists and the like can be appropriately selected for use. For example, the same groups as those described above as the "aliphatic cyclic groups" can be used.

Further, as the acetal-type, acid dissociable group, groups represented by general formula (p2) shown below can also be used.

[Chemical Formula 10]

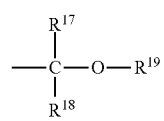

(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and $R^{17}$ is bonded to $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable. It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and $R^{19}$ may be bonded to $R^{17}$.

In such a case, a cyclic group is formed by $R^{17}$, $R^{19}$, the oxygen atom having $R^{19}$ bonded thereto and the carbon atom having the oxygen atom and $R^{17}$ bonded thereto. Such a cyclic group is preferably a 4- to 7-membered ring, and more preferably a 4- to 6-membered ring. Specific examples of the cyclic group include a tetrahydropyranyl group and a tetrahydrofuranyl group.

As the structural unit (a11), it is preferable to use at least one member selected from the group consisting of structural units represented by general formula (a1-0-1) shown below and structural units represented by general formula (a1-0-2) shown below.

[Chemical Formula 11]

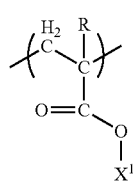

(a1-0-1)

In the formula, R represents a hydrogen atom, an alkyl group of 1 to 5 carbon atoms or a halogenated alkyl group of 1 to 5 carbon atoms; and $X^1$ represents an acid dissociable group.

[Chemical Formula 12]

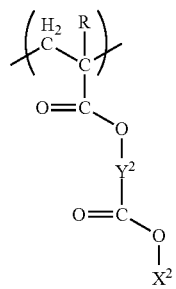

(a1-0-2)

In the formula, R represents a hydrogen atom, an alkyl group of 1 to 5 carbon atoms or a halogenated alkyl group of 1 to 5 carbon atoms; $X^2$ represents an acid dissociable group; and $Y^2$ represents a divalent linking group.

In general formula (a1-0-1), as the alkyl group of 1 to 5 carbon atoms or halogenated alkyl group of 1 to 5 carbon atoms for R, the same alkyl groups of 1 to 5 carbon atoms or halogenated alkyl groups of 1 to 5 carbon atoms as those defined above for the substituent which may be bonded to the carbon atom on the α-position can be used.

$X^1$ is not particularly limited as long as it is an acid dissociable group. Examples thereof include the aforementioned tertiary alkyl ester-type acid dissociable groups and acetal-type acid dissociable groups, and tertiary alkyl ester-type acid dissociable groups are preferable.

In general formula (a1-0-2), R is the same as defined above. $X^2$ is the same as defined for $X^1$ in general formula (a1-0-1).

Examples of the divalent linking group for $Y^2$ include an alkylene group, a divalent aliphatic cyclic group and a divalent linking group containing a hetero atom.

As the aliphatic cyclic group, the same groups as those listed above in connection with the explanation of "aliphatic cyclic group" can be used, with the exception that two or more hydrogen atoms have been removed therefrom.

When $Y^2$ represents an alkylene group, it preferably has 1 to 10 carbon atoms, more preferably 1 to 6 carbon atoms, still more preferably 1 to 4 carbon atoms, and most preferably 1 to 3 carbon atoms.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples of the divalent linking groups containing a hetero atom include —O—, —C(=O)—O—, —C(=O)—, —O—C(=O)—O—, —C(=O)—NH—, —NH— (H may be replaced with a substituent such as an alkyl group, an acyl group or the like), —S—, —S(=O)$_2$—, —S(=O)$_2$—O—, groups represented by general formula "-$A^2$-O(oxygen atom)-$B^2$— (in the formulas, each of $A^2$ and $B^2$ independently represents a divalent hydrocarbon group which may have a substituent)", "-[$A^2$-C(=O)—O]$_m$—$B^2$—" or "-$A^2$-O—C(=O)—$B^2$—", and suitable combinations of an alkylene group with divalent linking groups containing a hetero atom.

When $Y^2$ represents —NH—, the substituent (an alkyl group, an acyl group or the like) preferably has 1 to 10 carbon atoms, more preferably 1 to 8 carbon atoms, and most preferably 1 to 5 carbon atoms.

When Y² is a group represented by formula "-A²-O—B²—", "-[A²-C(=O)—O]ₘ—B²—" or "-A²-O—C(=O)—B²—", each of A² and B² independently represents a divalent hydrocarbon group which may have a substituent, and m represents an integer of 0 to 3.

The description that the hydrocarbon group "may have a substituent" means that some or all of the hydrogen atoms within the hydrocarbon group may be substituted with an atom other than a hydrogen atom or with a group.

The hydrocarbon group for A² may be either an aliphatic hydrocarbon group, or an aromatic hydrocarbon group. An "aliphatic hydrocarbon group" refers to a hydrocarbon group that has no aromaticity.

The aliphatic hydrocarbon group for A² may be either saturated or unsaturated. In general, the aliphatic hydrocarbon group is preferably saturated.

As specific examples of the aliphatic hydrocarbon group for A², a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 8 carbon atoms, still more preferably 2 to 5 carbon atoms, and most preferably 2 carbon atoms.

As a linear aliphatic hydrocarbon group, a linear alkylene group is preferable, and specific examples include a methylene group, an ethylene group [—(CH₂)₂—], a trimethylene group [—(CH₂)₃—], a tetramethylene group [—(CH₂)₄—] and a pentamethylene group [—(CH₂)₅—].

As the branched aliphatic hydrocarbon group, a branched alkylene group is preferable, and specific examples include various alkylalkylene groups, including alkylmethylene groups such as —CH(CH₃)—, —CH(CH₂CH₃)—, —C(CH₃)₂—, —C(CH₃)(CH₂CH₃)—, —C(CH₃)(CH₂CH₂CH₃)— and —C(CH₂CH₃)₂—; alkylethylene groups such as —CH(CH₃)CH₂—, —CH(CH₃)CH(CH₃)—, —C(CH₃)₂CH₂— and —CH(CH₂CH₃)CH₂—; alkyltrimethylene groups such as —CH(CH₃)CH₂CH₂— and —CH₂CH(CH₃)CH₂—; and alkyltetramethylene groups such as —CH(CH₃)CH₂CH₂CH₂— and —CH₂CH(CH₃)CH₂CH₂—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated alkyl group of 1 to 5 carbon atoms, and an oxygen atom (=O).

Examples of the aliphatic hydrocarbon group containing a ring in the structure thereof include cyclic aliphatic hydrocarbon groups (groups in which two hydrogen atoms have been removed from an aliphatic hydrocarbon ring), and groups in which this type of cyclic aliphatic hydrocarbon group is either bonded to the terminal of an aforementioned chain-like aliphatic hydrocarbon group, or interposed within the chain of an aforementioned chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

As A², a linear aliphatic hydrocarbon group is preferred, a linear alkylene group is more preferred, a linear alkylene group of 2 to 5 carbon atoms is still more preferred, and an ethylene group is particularly desirable.

Examples of the hydrocarbon groups for B² include the same divalent hydrocarbon groups as those described above for A².

As B², a linear or branched aliphatic hydrocarbon group is preferable, and a methylene group or an alkylmethylene group is particularly desirable.

The alkyl group within the alkylmethylene group is preferably a linear alkyl group of 1 to 5 carbon atoms, more preferably a linear alkyl group of 1 to 3 carbon atoms, and most preferably a methyl group.

Further, in the group represented by the formula -[A²-C(=O)—O]ₘ—B²—, m represents an integer of 0 to 3, preferably an integer of 0 to 2, more preferably 0 or 1, and most preferably 1.

Specific examples of the structural unit (a11) include structural units represented by general formulas (a1-1) to (a1-4) shown below.

[Chemical Formula 13]

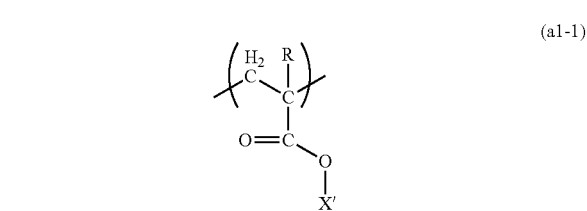

(a1-1)

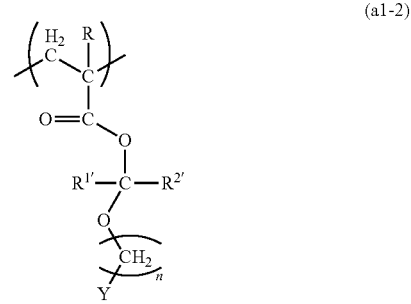

(a1-2)

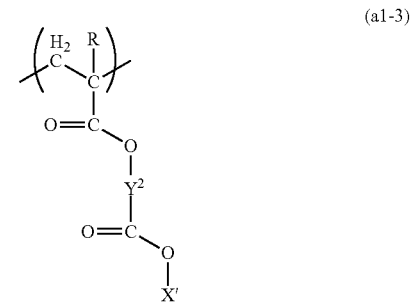

(a1-3)

-continued (a1-4)

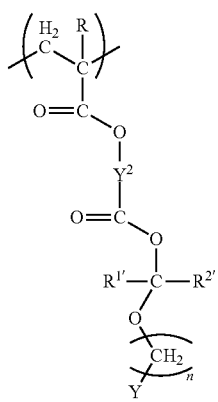

In the formulas, X' represents a tertiary alkyl ester-type acid dissociable group; Y represents an alkyl group of 1 to 5 carbon atoms or an aliphatic cyclic group; n represents an integer of 0 to 3; $Y^2$ represents a divalent linking group; R is the same as defined above; and each of $R^{1'}$ and $R^{2'}$ independently represents a hydrogen atom or an alkyl group of 1 to 5 carbon atoms.

In the above formulas, examples of the tertiary alkyl ester-type acid dissociable group for X' include the same tertiary alkyl ester-type acid dissociable groups as those described above for $X^1$.

As $R^{1'}$, $R^{2'}$, n and Y are respectively the same as defined for $R^{1'}$, $R^{2'}$, n and Y in general formula (p1) described above in connection with the "acetal-type acid dissociable group".

As examples of $Y^2$, the same groups as those described above for $Y^2$ in general formula (a1-0-2) can be given.

Specific examples of structural units represented by general formula (a1-1) to (a1-4) are shown below.

In the formulas shown below, $R^\alpha$ represents a hydrogen atom, a methyl group or a trifluoromethyl group.

[Chemical Formula 14]

(a1-1-1)

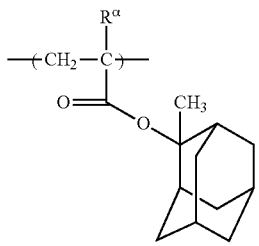

(a1-1-2)

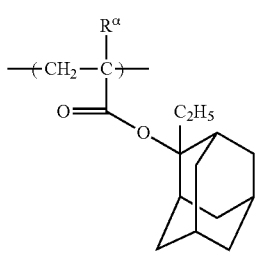

(a1-1-3)

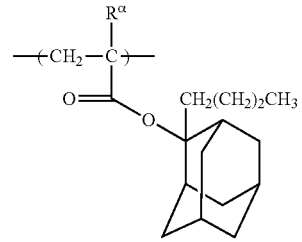

(a1-1-4)

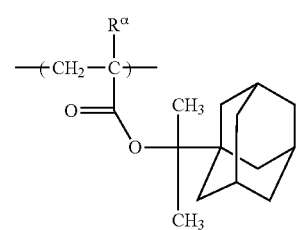

(a1-1-5)

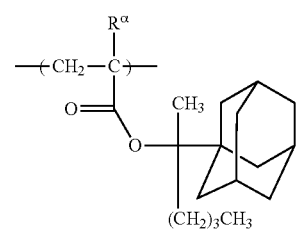

(a1-1-6)

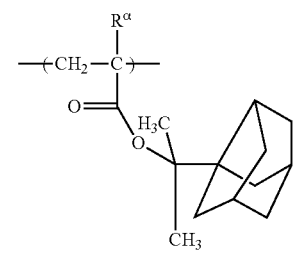

(a1-1-7)

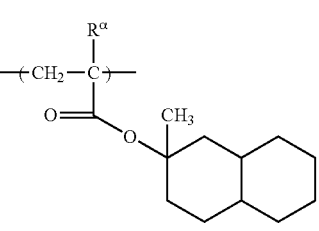

(a1-1-8)

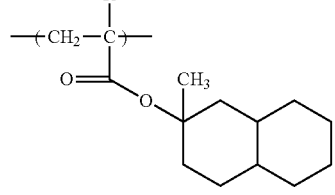

(a1-1-9)

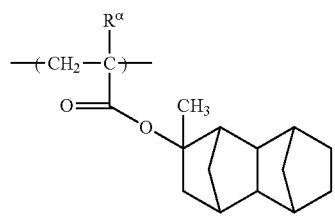

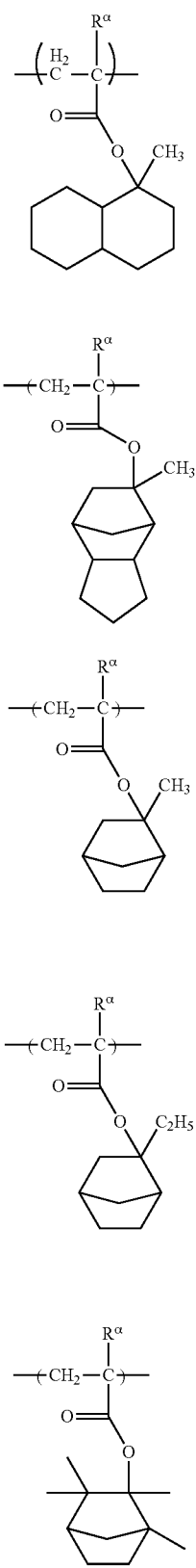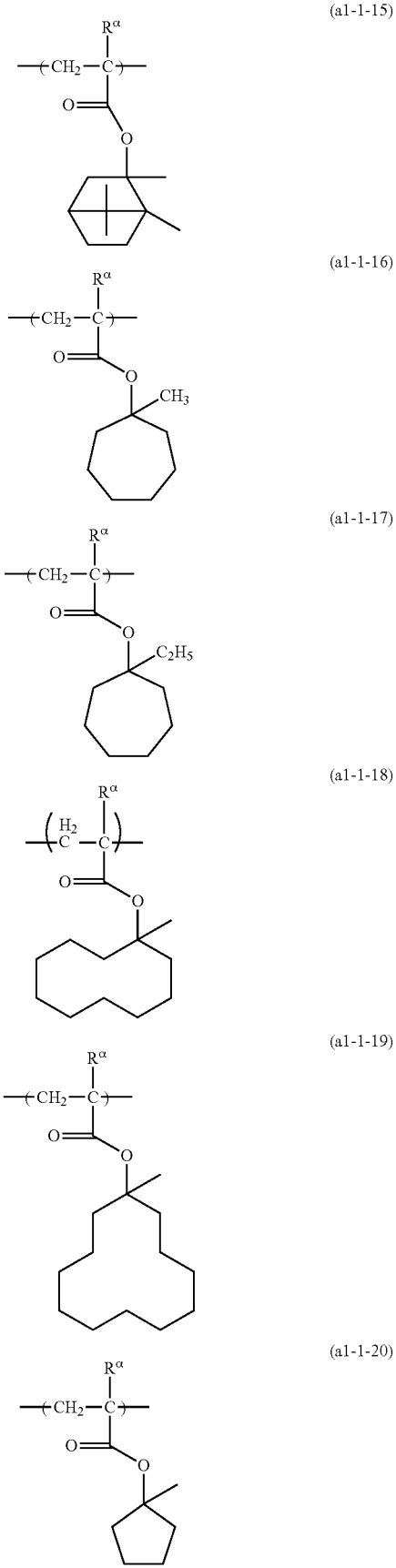

(a1-1-21)
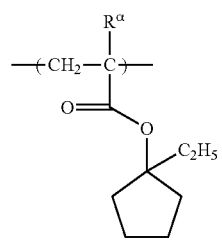
[Chemical Formula 16]
(a1-1-22)
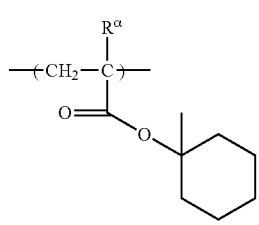
(a1-1-23)
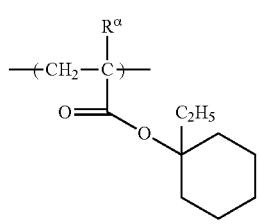
(a1-1-24)
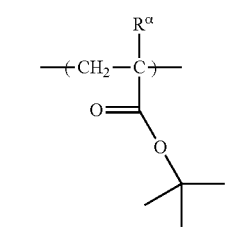
(a1-1-25)
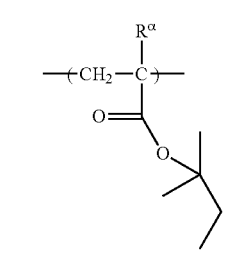
(a1-1-26)
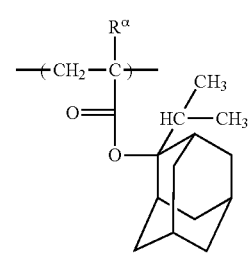
(a1-1-27)
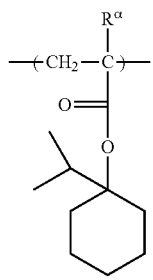
(a1-1-28)
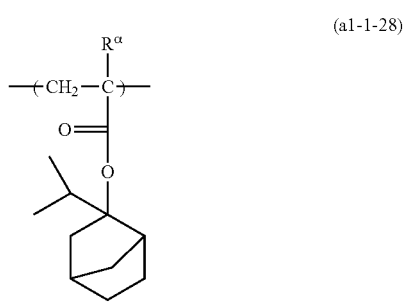
(a1-1-29)
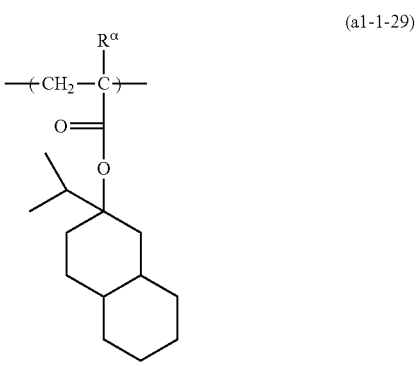
(a1-1-30)
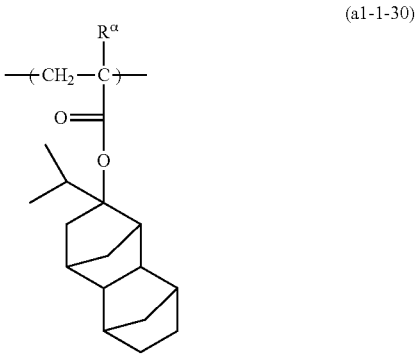
(a1-1-31)
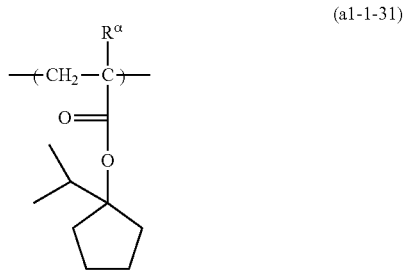

(a1-1-32)
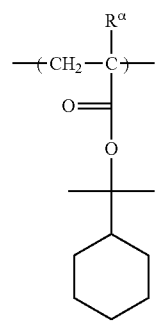
[Chemical Formula 17]
(a1-2-1)
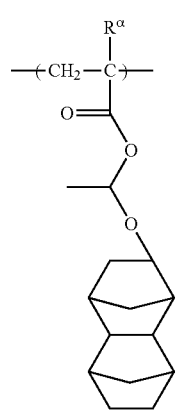
(a1-2-2)
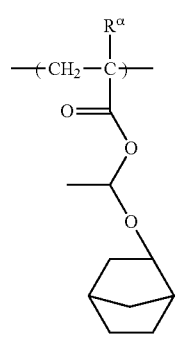
(a1-2-3)
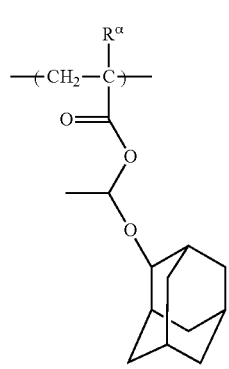
(a1-2-4)
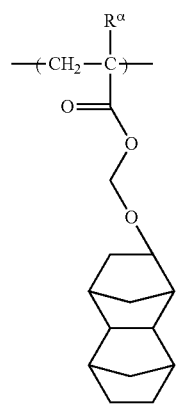
(a1-2-5)
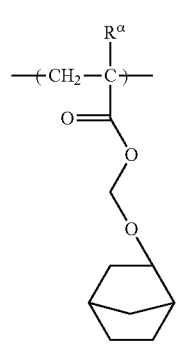
(a1-2-6)
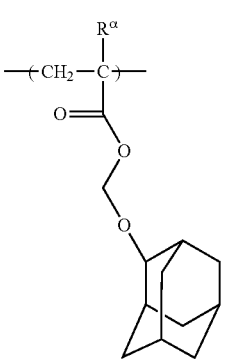
(a1-2-7)
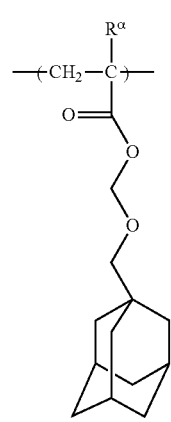

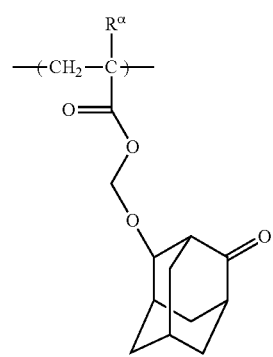 (a1-2-8)
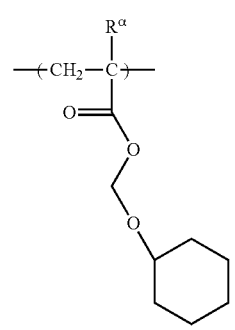 (a1-2-9)
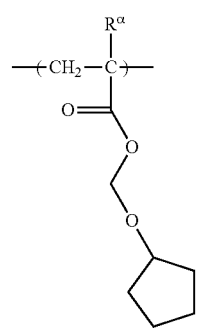 (a1-2-10)
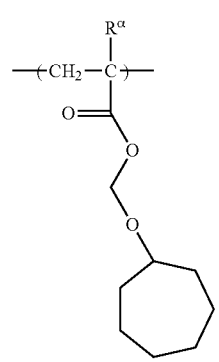 (a1-2-11)
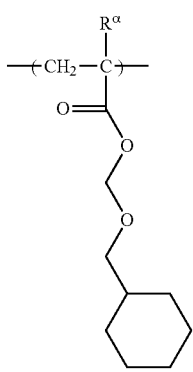 (a1-2-12)
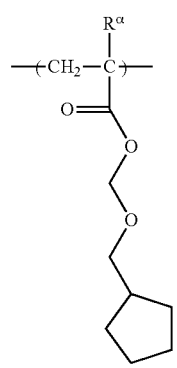 (a1-2-13)
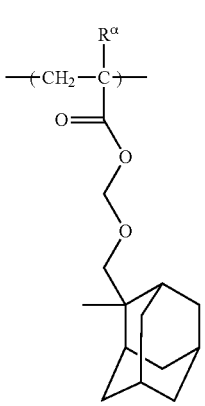 (a1-2-14)
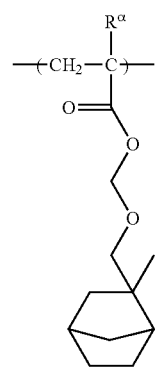 (a1-2-15)

(a1-2-16)
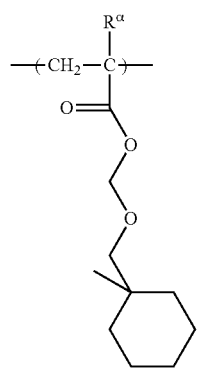
(a1-2-17)
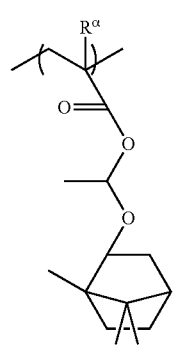
(a1-2-18)
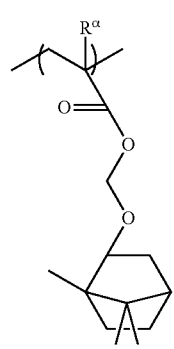
(a1-2-19)
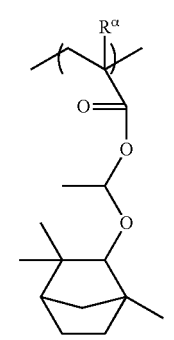
(a1-2-20)
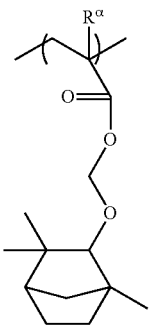
(a1-2-21)
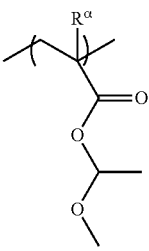
(a1-2-22)
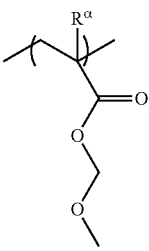
(a1-2-23)
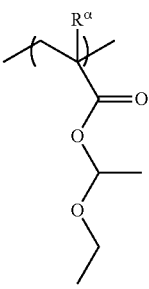
(a1-2-24)
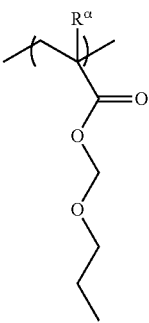

[Chemical Formula 18]
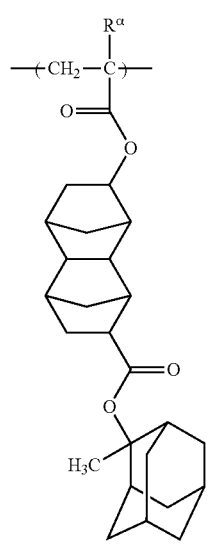
(a1-3-1)
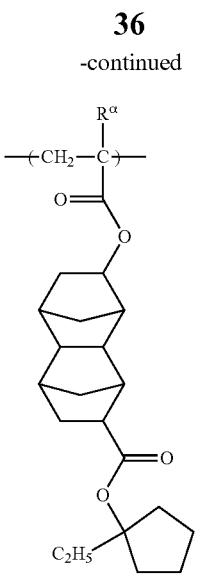
(a1-3-4)
(a1-3-2)
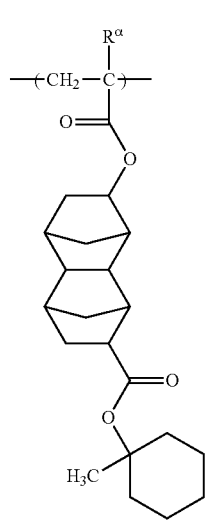
(a1-3-5)
(a1-3-3)
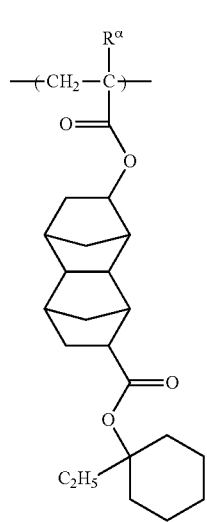
(a1-3-6)

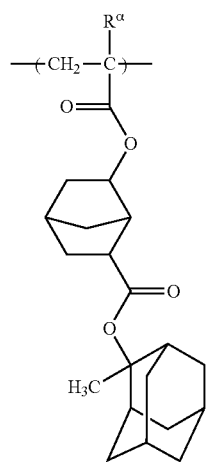
(a1-3-7)
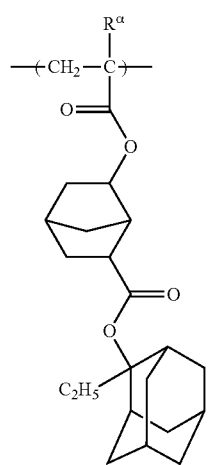
(a1-3-8)
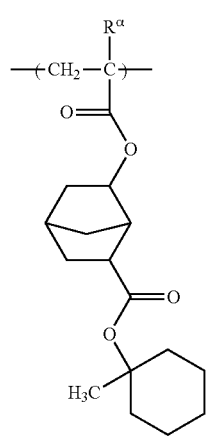
(a1-3-9)
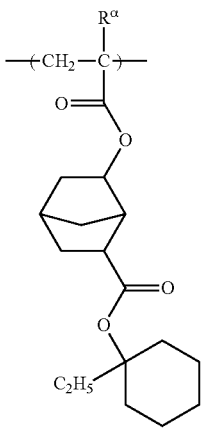
(a1-3-10)
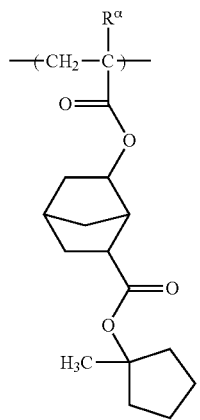
(a1-3-11)
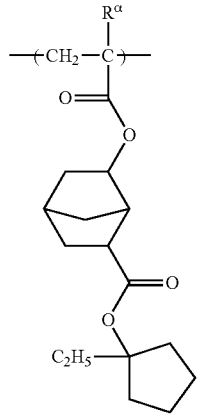
(a1-3-12)
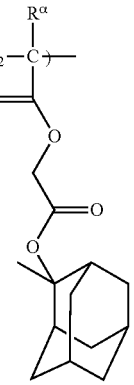
(a1-3-13)

(a1-3-14)
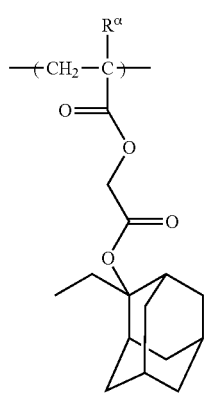
(a1-3-15)
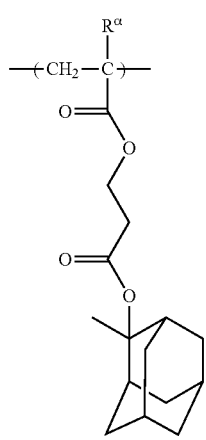
(a1-3-16)
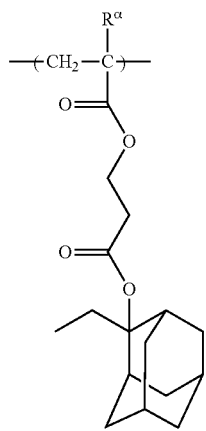
(a1-3-17)
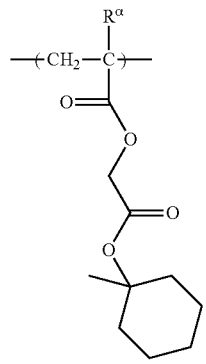
(a1-3-18)
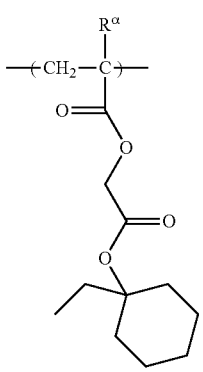
[Chemical Formula 19]
(a1-3-19)
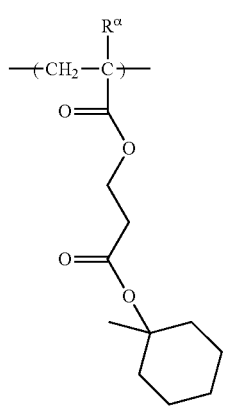
(a1-3-20)
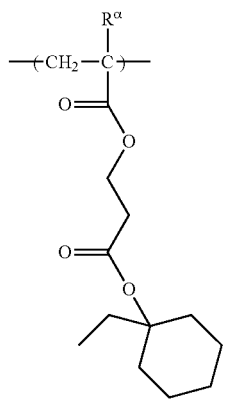
(a1-3-21)
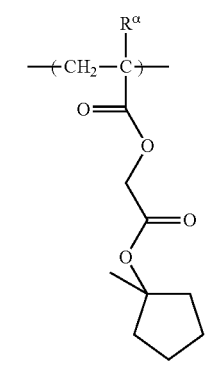

[Chemical Formula 20]
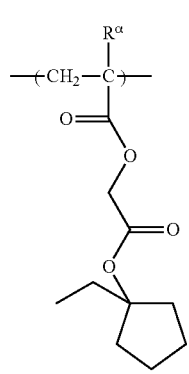 (a1-3-22)
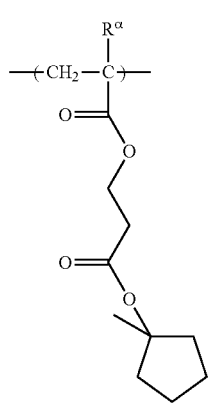 (a1-3-23)
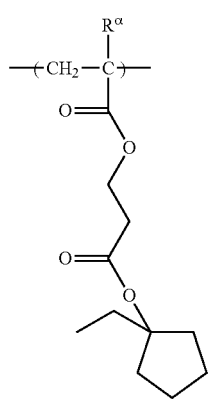 (a1-3-24)
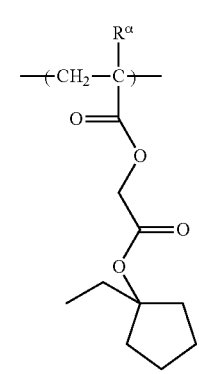 (a1-3-25)
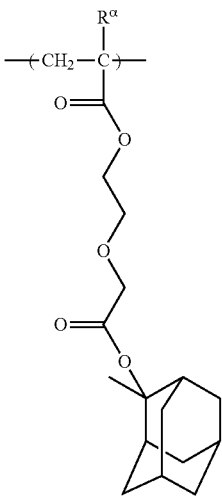 (a1-3-26)
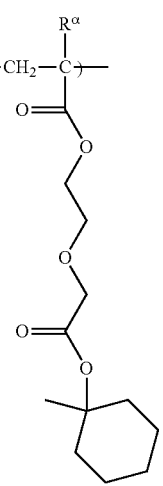 (a1-3-27)

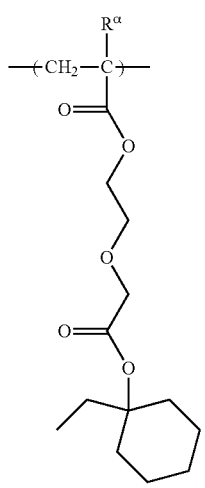
(a1-3-28)
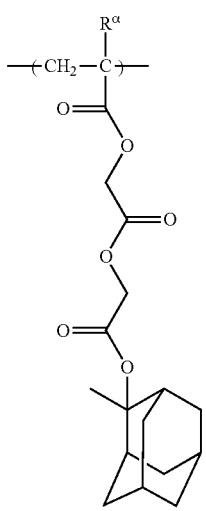
(a1-3-29)
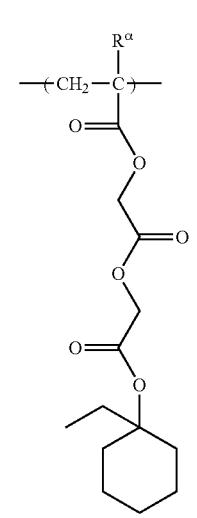
(a1-3-30)
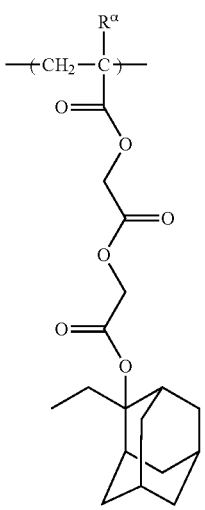
(a1-3-31)
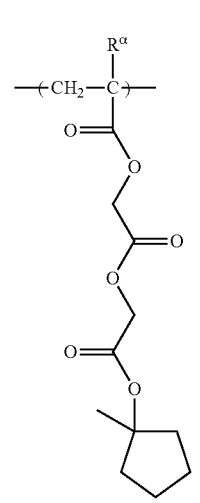
(a1-3-32)
[Chemical Formula 21]
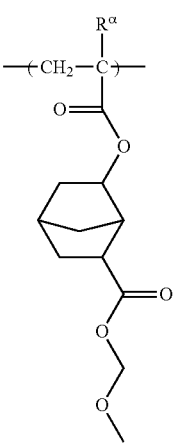
(a1-4-1)

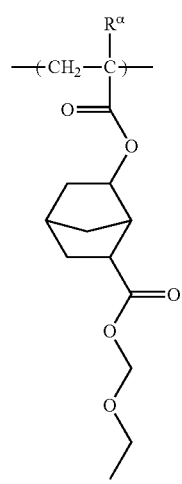 (a1-4-2)
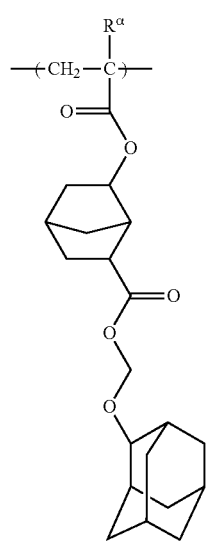 (a1-4-3)
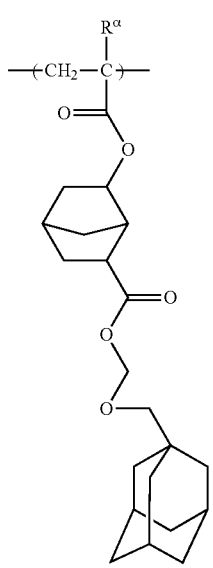 (a1-4-4)
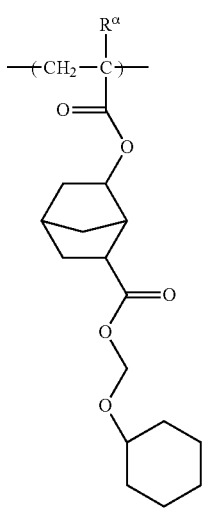 (a1-4-5)
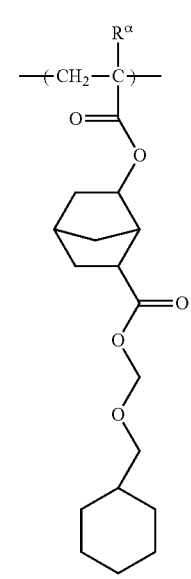 (a1-4-6)
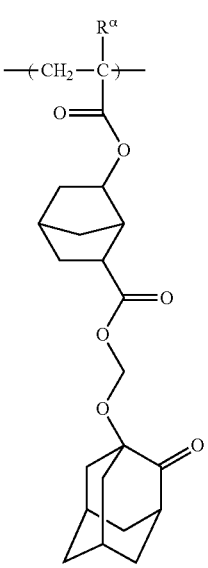 (a1-4-7)

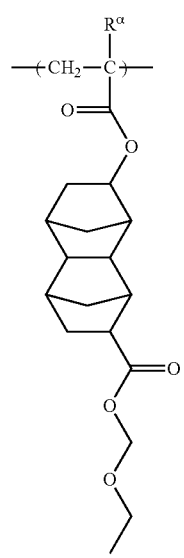
(a1-4-8)
(a1-4-9)
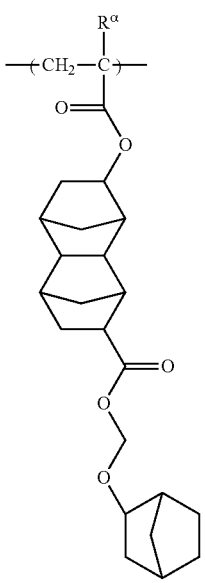
(a1-4-10)
(a1-4-11)

-continued

As the structural unit (a11), one type of structural unit may be used alone, or two or more types of structural units may be used in combination.

Among these, structural units represented by general formula (a1-1), (a1-2) or (a1-3) are preferable. More specifically, at least one structural unit selected from the group consisting of structural units represented by formulas (a1-1-1) to (a1-1-5), (a1-1-20) to (a1-1-23), (a1-2-1) to (a1-2-24), (a1-3-25) to (a1-3-28) and (a1-1-32) is more preferable.

Furthermore, as the structural unit (a11), structural units represented by general formula (a1-1-01) shown below which includes the structural units represented by formulas (a1-1-1) to (a1-1-3) and (a1-1-26), structural units represented by general formula (a1-1-02) shown below which includes the structural units represented by formulas (a1-1-16) to (a1-1-17) and (a1-1-20) to (a1-1-23), structural units represented by general formula (a1-2-01) shown below which includes the structural units represented by formulas (a1-2-3), (a1-2-6) and (a1-2-14), structural units represented by general formula (a1-3-01)

shown below which includes the structural units represented by formulas (a1-3-25) to (a1-3-26), structural units represented by general formula (a1-3-02) shown below which includes the structural units represented by formulas (a1-3-27) to (a1-3-28), or structural units represented by general formula (a1-3-03) shown below which includes the structural units represented by formulas (a1-3-29) to (a1-3-30) are also particularly desirable.

[Chemical Formula 22]

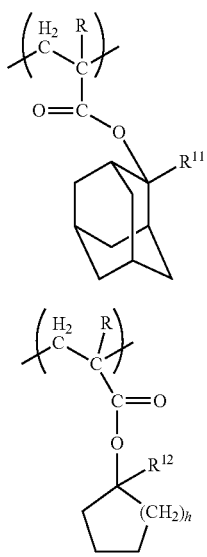

(a1-1-01)

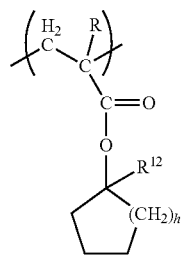

(a1-1-02)

In the formulas, each R independently represents a hydrogen atom, an alkyl group of 1 to 5 carbon atoms or a halogenated alkyl group of 1 to 5 carbon atoms; $R^{11}$ represents an alkyl group of 1 to 5 carbon atoms; $R^{12}$ represents an alkyl group of 1 to 7 carbon atoms; and h represents an integer of 1 to 6.

In general formula (a1-1-01), R is the same as defined above. As the alkyl group of 1 to 5 carbon atoms for $R^{11}$, the same alkyl groups of 1 to 5 carbon atoms as those described above for R can be used, and a methyl group, an ethyl group or an isopropyl group is preferable.

In general formula (a1-1-02), R is the same as defined above. As the alkyl group of 1 to 5 carbon atoms for $R^{12}$, the same alkyl groups of 1 to 5 carbon atoms as those described above for R can be used, and a methyl group, an ethyl group or an isopropyl group is preferable. h is preferably 1 or 2, and most preferably 2.

[Chemical Formula 23]

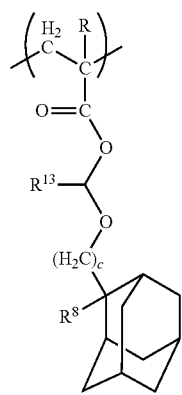

(a1-2-01)

In the formula, R represents a hydrogen atom, an alkyl group of 1 to 5 carbon atoms or a halogenated alkyl group of 1 to 5 carbon atoms; $R^{13}$ represents a hydrogen atom or a methyl group; $R^8$ represents a hydrogen atom or an alkyl group of 1 to 5 carbon atoms; and c represents an integer of 0 to 3.

In general formula (a1-2-01), R is the same as defined above. As the alkyl group of 1 to 5 carbon atoms for $R^8$, the same alkyl groups of 1 to 5 carbon atoms as those described above for R can be used, and a methyl group, an ethyl group or an isopropyl group is preferable. c is preferably 0 to 2, and more preferably 0 or 1.

[Chemical Formula 24]

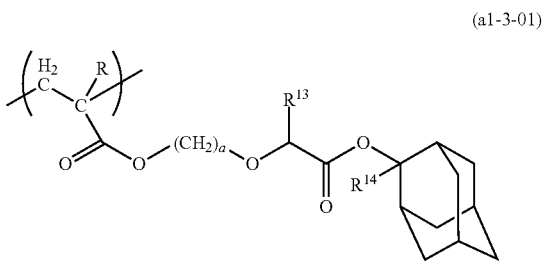

(a1-3-01)

In the formula, R represents a hydrogen atom, an alkyl group of 1 to 5 carbon atoms or a halogenated alkyl group of 1 to 5 carbon atoms; $R^{14}$ is the same as defined above; $R^{13}$ represents a hydrogen atom or a methyl group; and a represents an integer of 1 to 10.

[Chemical Formula 25]

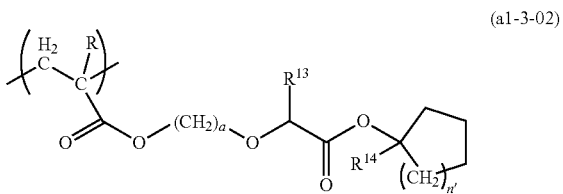

(a1-3-02)

In the formula, R represents a hydrogen atom, an alkyl group of 1 to 5 carbon atoms or a halogenated alkyl group of 1 to 5 carbon atoms; $R^{14}$ is the same as defined above; $R^{13}$ represents a hydrogen atom or a methyl group; a represents an integer of 1 to 10; and n' represents an integer of 1 to 6.

[Chemical Formula 26]

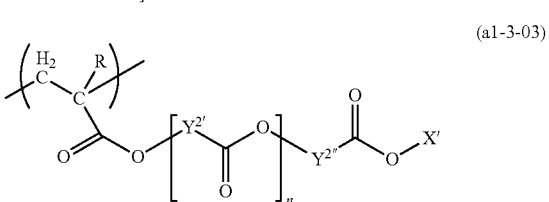

(a1-3-03)

In the formula, R is the same as defined above; each of $Y^{2'}$ and $Y^{2''}$ independently represents a divalent linking group; X' represents an acid dissociable group; and n represents an integer of 0 to 3.

In the above general formulas (a1-3-01) to (a1-3-03), R is the same as defined above.

$R^{13}$ is preferably a hydrogen atom.

n' is preferably 1 or 2, and most preferably 2.

a is preferably an integer of 1 to 8, more preferably an integer of 2 to 5, and most preferably 2.

As the divalent linking group for $Y^{2'}$ and $Y^{2''}$, the same groups as those described above for $Y^2$ in general formula (a1-3) can be used.

As $Y^{2'}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2''}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable group for X', the same groups as those described above can be used. X' is preferably a tertiary alkyl ester-type acid dissociable group, more preferably the aforementioned group (i) which has a tertiary carbon atom on the ring structure of a monovalent aliphatic cyclic group. Among the aforementioned groups (i), a group represented by general formula (1-1) above is preferable.

n represents an integer of 0 to 3, preferably an integer of 0 to 2, more preferably 0 or 1, and most preferably 1.

In the component (A1), the amount of the structural unit (a11) based on the combined total of all structural units constituting the component (A1) is preferably 5 to 80 mol %, more preferably 10 to 80 mol %, and still more preferably 15 to 75 mol %. By making the amount of the structural unit (a11) at least as large as the lower limit of the above-mentioned range, a pattern can be easily formed using a resist composition prepared from the component (A1). On the other hand, by making the amount of the structural unit (a11) no more than the upper limit of the above-mentioned range, a good balance can be achieved with the other structural units.
(Structural Unit (a12))

The structural unit (a12) is a structural unit derived from a hydroxystyrene derivative, and is also a structural unit containing an acid decomposable group that exhibits increased polarity by the action of acid. Examples of the acid decomposable group for the structural unit (a12) include the same groups as those described above for the structural unit (a11).

Examples of the acid decomposable group include groups in which the hydrogen atoms of —OH moiety within the phenolic hydroxyl groups for the structural unit (a12) have been substituted with acetal-type acid dissociable groups; and groups in which the hydrogen atoms of —OH moiety within the phenolic hydroxyl groups for the structural unit (a12) have been substituted with tertiary alkyl ester-type acid dissociable groups or acetal-type acid dissociable groups, through —C(=O)O— or a linking group such as (—$Y^2$—C(=O)—O—) in the above formula (a1-0-2).

In the component (A1), the amount of the structural unit (a12) based on the combined total of all structural units constituting the component (A1) is preferably 5 to 80 mol %, more preferably 10 to 80 mol %, and still more preferably 15 to 75 mol %. By making the amount of the structural unit (a12) at least as large as the lower limit of the above-mentioned range, a pattern can be easily formed using a resist composition prepared from the component (A1). On the other hand, by making the amount of the structural unit (a12) no more than the upper limit of the above-mentioned range, a good balance can be achieved with the other structural units.
(Structural Unit (a2))

The structural unit (a2) is at least one structural unit selected from the group consisting of structural units containing a —$SO_2$-containing cyclic group and derived from an acrylate ester in which a hydrogen atom bonded to the carbon atom on the α-position may be substituted with a substituent (hereafter, referred to as "structural unit (a2$^S$)") and structural units containing a lactone-containing cyclic group and derived from an acrylate ester in which a hydrogen atom bonded to the carbon atom on the α-position may be substituted with a substituent (hereafter, referred to as "structural unit (a2$^L$)").

By virtue of the structural unit (a2) containing a —$SO_2$-containing cyclic group or a lactone-containing cyclic group, a positive resist composition containing the component (A1) including the structural unit (a2) is capable of improving the adhesion of a resist film to a substrate, and increasing the compatibility with the developing solution containing water (especially, in the case of alkali developing process), thereby contributing to improvement of lithography properties.
—Structural Unit (a2$^S$):

The structural unit (a2$^S$) is a structural unit containing a —$SO_2$-containing cyclic group and derived from an acrylate ester in which a hydrogen atom bonded to the carbon atom on the α-position may be substituted with a substituent.

Here, a "—$SO_2$-containing cyclic group" refers to a cyclic group having a ring that contains —$SO_2$— within the ring skeleton thereof, i.e., a cyclic group in which the sulfur atom (S) within —$SO_2$— forms part of the ring skeleton of the cyclic group. This ring that contains —$SO_2$— within the ring skeleton thereof is counted as the first ring. A cyclic group in which the only ring structure is this ring is referred to as a monocyclic group, and a group containing other ring structures is described as a polycyclic group regardless of the structure of the other rings. The —$SO_2$-containing cyclic group may be either a monocyclic group or a polycyclic group.

As the —$SO_2$-containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

The —$SO_2$-containing cyclic group preferably has 3 to 30 carbon atoms, more preferably 4 to 20 carbon atoms, still more preferably 4 to 15 carbon atoms, and most preferably 4 to 12 carbon atoms. Herein, the number of carbon atoms refers to the number of carbon atoms constituting the ring skeleton, excluding the number of carbon atoms within a substituent.

The —$SO_2$-containing cyclic group may be either a —$SO_2$-containing aliphatic cyclic group or a —$SO_2$-containing aromatic cyclic group, but is preferably a —$SO_2$-containing aliphatic cyclic group.

Examples of the —$SO_2$-containing aliphatic cyclic group include aliphatic cyclic groups in which part of the carbon atoms constituting the ring skeleton thereof has been substituted with a —$SO_2$— group or a —O—$SO_2$— group and has at least one hydrogen atom removed from the aliphatic hydrocarbon ring. Specific examples include an aliphatic hydrocarbon ring in which a —$CH_2$— group constituting the ring skeleton thereof has been substituted with a —$SO_2$— group and has at least one hydrogen atom removed therefrom; and an aliphatic hydrocarbon ring in which a —$CH_2$—$CH_2$— group constituting the ring skeleton thereof has been substituted with a —O—$SO_2$— group and has at least one hydrogen atom removed therefrom.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic alicyclic hydrocarbon group, a group in which one hydrogen atom has been removed from a monocycloalkane of 3 to 6 carbon atoms is preferable. Examples of the monocycloalkane include cyclopentane and cyclohexane. As the polycyclic alicyclic hydrocarbon group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The —SO2-containing cyclic group may have a substituent. Examples of the substituent include an alkyl group, an alkoxy group, a halogen atom, a halogenated alkyl group, a hydroxy group, an oxygen atom (=O), —COOR", —OC(=O)R", a hydroxyalkyl group and a cyano group.

The alkyl group for the substituent is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear alkoxy group or a branched alkoxy group. Specific examples of the alkoxy group include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(=O)R" group, R" represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

In those cases where R" represents a cyclic alkyl group, the cyclic alkyl group preferably has 3 to 15 carbon atoms, more preferably 4 to 12 carbon atoms, and most preferably 5 to 10 carbon atoms. As examples of the cyclic alkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxyl group.

More specific examples of the —SO$_2$-containing cyclic group include groups represented by general formulas (3-1) to (3-4) shown below.

[Chemical Formula 27]

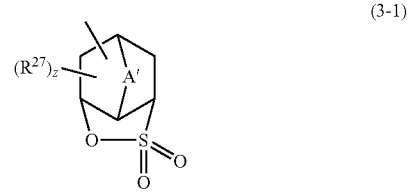

(3-1)

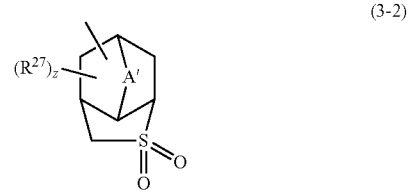

(3-2)

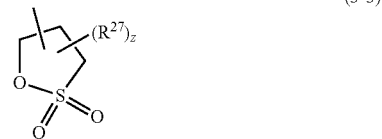

(3-3)

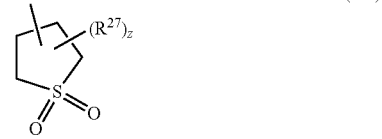

(3-4)

In the formulas, A' represents an oxygen atom, a sulfur atom or an alkylene group of 1 to 5 carbon atoms which may contain an oxygen atom or a sulfur atom; z represents an integer of 0 to 2; and R$^{27}$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group.

In general formulas (3-1) to (3-4) above, A' represents an oxygen atom (—O—), a sulfur atom (—S—) or an alkylene group of 1 to 5 carbon atoms which may contain an oxygen atom or a sulfur atom.

As the alkylene group of 1 to 5 carbon atoms represented by A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—.

A' is preferably an alkylene group of 1 to 5 carbon atoms or —O—, is more preferably an alkylene group of 1 to 5 carbon atoms, and is most preferably a methylene group.

z represents an integer of 0 to 2, and is most preferably 0.

When z is 2, the plurality of $R^{27}$ may be the same or different from each other.

As the alkyl group, alkoxy group, halogenated alkyl group, —COOR", —OC(=O)R" and hydroxyalkyl group for $R^{27}$, the same alkyl groups, alkoxy groups, halogenated alkyl groups, —COOR", —OC(=O)R" and hydroxyalkyl groups as those described above as the substituent which the —SO$_2$-containing cyclic group can be used.

Specific examples of the cyclic groups represented by general formulas (3-1) to (3-4) are shown below. In the formulas shown below, "Ac" represents an acetyl group.

[Chemical Formula 28]

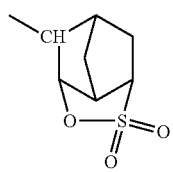
(3-1-1)

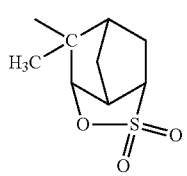
(3-1-2)

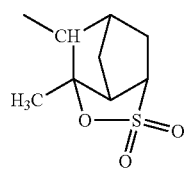
(3-1-3)

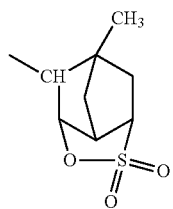
(3-1-4)

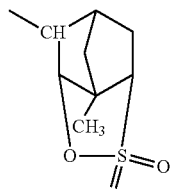
(3-1-5)

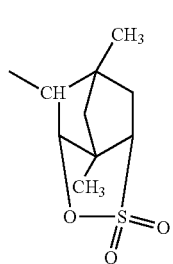
(3-1-6)

-continued

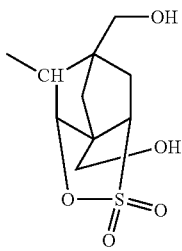
(3-1-7)

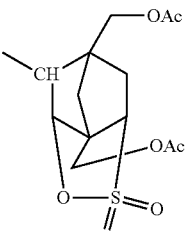
(3-1-8)

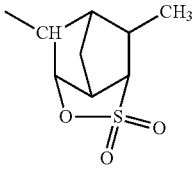
(3-1-9)

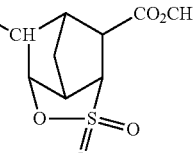
(3-1-10)

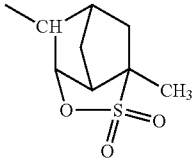
(3-1-11)

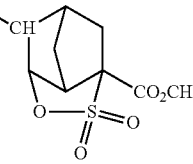
(3-1-12)

[Chemical Formula 29]

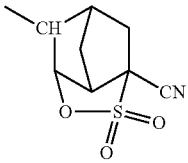
(3-1-13)

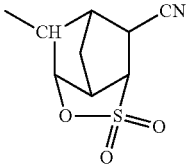
(3-1-14)

(3-1-15) 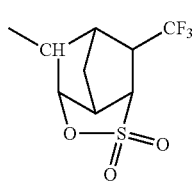
(3-1-16) 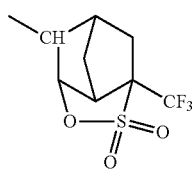
(3-1-17) 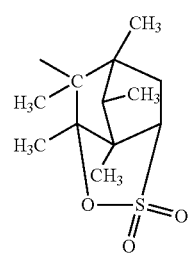
[Chemical Formula 30]
(3-1-18) 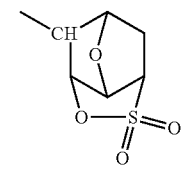
(3-1-19) 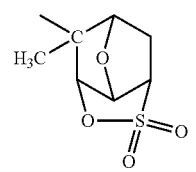
(3-1-20) 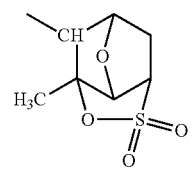
(3-1-21) 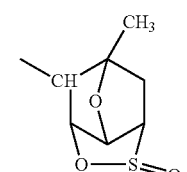
(3-1-22) 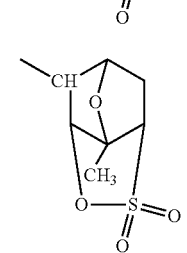
(3-1-23) 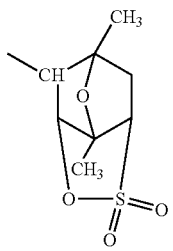
(3-1-24) 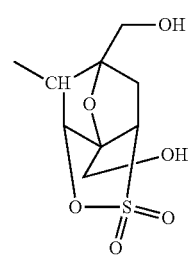
(3-1-25) 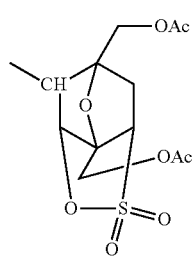
[Chemical Formula 31]
(3-1-26) 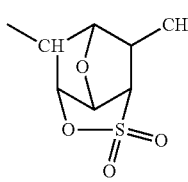
(3-1-27) 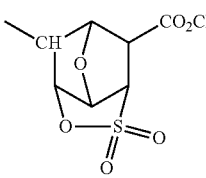
(3-1-28) 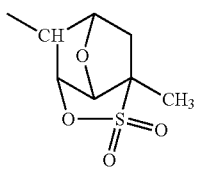
(3-1-29) 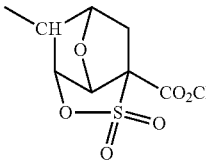

-continued

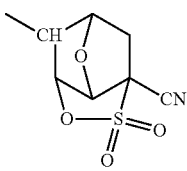
(3-1-30)

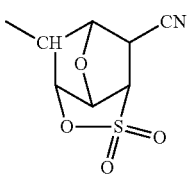
(3-1-31)

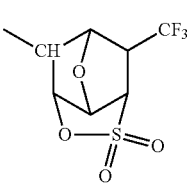
(3-1-32)

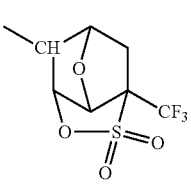
(3-1-33)

[Chemical Formula 32]

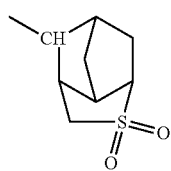
(3-2-1)

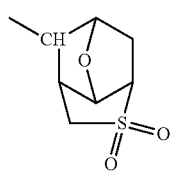
(3-2-2)

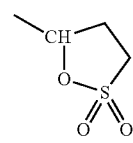
(3-3-1)

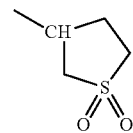
(3-4-1)

Of the various possibilities described above, as the —SO$_2$-containing cyclic group, a group represented by the aforementioned general formula (3-1) is preferable, at least one member selected from the group consisting of groups represented by the aforementioned chemical formulas (3-1-1), (3-1-18), (3-3-1) and (3-4-1) is more preferable, and a group represented by the aforementioned chemical formula (3-1-1) is most preferable.

More specific examples of the structural unit (a2$^S$) include structural units represented by general formula (a2-0) shown below.

[Chemical Formula 33]

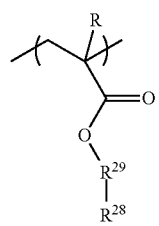
(a2-0)

In the formula, R represents a hydrogen atom, an alkyl group of 1 to 5 carbon atoms or a halogenated alkyl group of 1 to 5 carbon atoms; $R^{28}$ represents a —SO$_2$-containing cyclic group; and $R^{29}$ represents a single bond or a divalent linking group.

In genera formula (a2-0), R is the same as defined above.
$R^{28}$ is the same as defined for the aforementioned —SO$_2$-containing group.

$R^{29}$ may be either a single bond or a divalent linking group. In terms of the effects of the present invention, a divalent linking group is preferable.

The divalent linking group for $R^{29}$ is not particularly limited. For example, the same divalent linking groups as those described for $Y^2$ in the above general formula (a1-0-2) can be used. Among these, an alkylene group or a divalent linking group containing an ester bond (—C(=O)—O—) is preferable.

As the alkylene group, a linear or branched alkylene group is preferable. Specific examples include the same linear alkylene groups and branched alkylene groups as those described above for the aliphatic hydrocarbon group represented by $Y^2$.

As the divalent linking group containing an ester bond, a group represented by general formula: —$R^{30}$—C(=O)—O— (in the formula, $R^{30}$ represents a divalent linking group) is particularly desirable. That is, the structural unit (a2$^S$) is preferably a structural unit represented by general formula (a2-0-1) shown below.

[Chemical Formula 34]

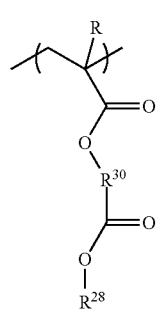
(a2-0-1)

In the formula, R and $R^{28}$ are the same as defined above; and $R^{30}$ represents a divalent linking group.

$R^{30}$ is not particularly limited, and examples thereof include the same divalent linking groups as those described for $Y^2$ in the above general formula (a1-0-2).

As the divalent linking group for $R^{30}$, a linear or branched alkylene group, a divalent alicyclic hydrocarbon group or a divalent linking group containing a hetero atom is preferable.

As the linear or branched alkylene group, the divalent alicyclic hydrocarbon group and the divalent linking group containing a hetero atom, the same linear or branched alkylene group, divalent alicyclic hydrocarbon group and divalent linking group containing a hetero atom as those described above for $Y^2$ can be mentioned.

Among these, a linear or branched alkylene group, or a divalent linking group containing an oxygen atom as a hetero atom is preferable.

As the linear alkylene group, a methylene group or an ethylene group is preferable, and a methylene group is particularly desirable.

As the branched alkylene group, an alkylmethylene group or an alkylethylene group is preferable, and —$CH(CH_3)$—, —$C(CH_3)_2$— or —$C(CH_3)_2CH_2$— is particularly desirable.

As the divalent linking group containing an oxygen atom, a divalent linking group containing an ether bond or an ester bond is preferable, and a group represented by the aforementioned formula -$A^2$-O—$B^2$—, -$[A^2$-$C(=O)$—$O]_m$—$B^2$— or -$A^2$-O—$C(=O)$—$B^2$— is more preferable.

Among these, a group represented by the formula -$A^2$-O—$C(=O)$—$B^2$— is preferable, and a group represented by the formula: —$(CH_2)_c$—$C(=O)$—O—$(CH_2)_d$— is particularly desirable. c represents an integer of 1 to 5, and preferably 1 or 2. d represents an integer of 1 to 5, and preferably 1 or 2.

In particular, as the structural unit ($a2^S$), a structural unit represented by general formula (a0-1-11) or (a0-1-12) shown below is preferable, and a structural unit represented by general formula (a0-1-12) shown below is more preferable.

[Chemical Formula 35]

(a0-1-11)

(a0-1-12)

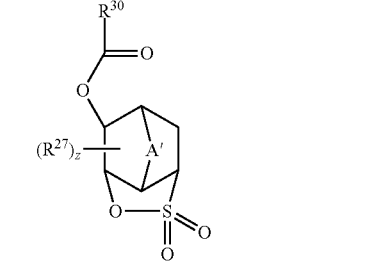

In the formulas, R, A', $R^{27}$, z and $R^{30}$ are the same as defined above.

In general formula (a0-1-11), A' is preferably a methylene group, an oxygen atom (—O—) or a sulfur atom (—S—).

As $R^{30}$, a linear or branched alkylene group or a divalent linking group containing an oxygen atom is preferable. As the linear or branched alkylene group and the divalent linking group containing an oxygen atom represented by $R^{30}$, the same linear or branched alkylene groups and the divalent linking groups containing an oxygen atom as those described above can be mentioned.

As the structural unit represented by general formula (a0-1-12), a structural unit represented by general formula (a0-1-12a) or (a0-1-12b) shown below is particularly desirable.

[Chemical Formula 36]

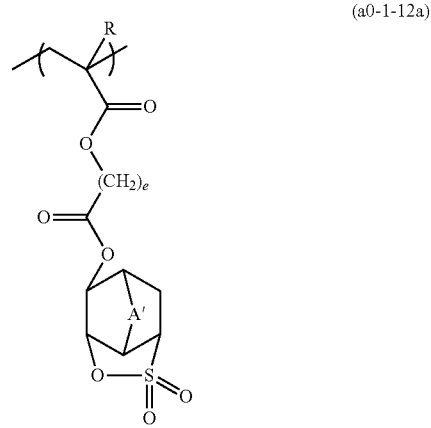

(a0-1-12a)

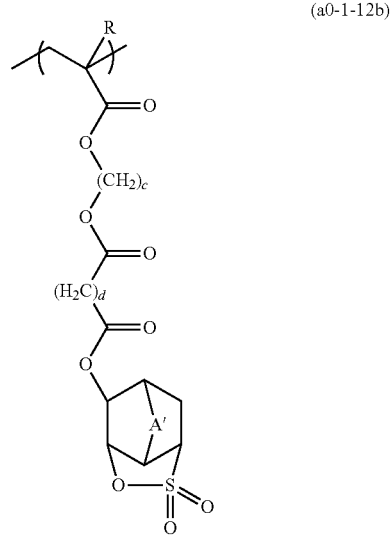

(a0-1-12b)

In the formulas, R and A' are the same as defined above; and each of c to e independently represents an integer of 1 to 3.

Structural Unit ($a2^L$):

The structural unit ($a2^L$) is a structural unit containing a lactone-containing cyclic group and derived from an acrylate ester in which an atom other than a hydrogen atom or a substituent may be bonded to the carbon atom on the α-position.

The term "lactone-containing cyclic group" refers to a cyclic group including a ring containing a —O—C(O)— group within the ring structure thereof (lactone ring). This "lactone ring" is counted as the first ring, so that a lactone-containing cyclic group in which the only ring structure is the lactone ring is referred to as a monocyclic group, and groups that also contain other ring structures are described as polycyclic groups regardless of the structure of the other rings. The lactone-containing cyclic group may be either a monocyclic group or a polycyclic group.

The lactone-containing cyclic group for the structural unit (a2$^L$) is not particularly limited, and an arbitrary group may be used. Specific examples of lactone-containing monocyclic groups include a group in which one hydrogen atom has been removed from a 4- to 6-membered lactone ring, such as a group in which one hydrogen atom has been removed from β-propionolactone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

Examples of the structural unit (a2$^L$) include structural units represented by the aforementioned general formula (a2-0) in which the R$^{28}$ group has been substituted with a lactone-containing cyclic group. Specific examples thereof include structural units represented by general formulas (a2-1) to (a2-5) shown below.

[Chemical Formula 37]

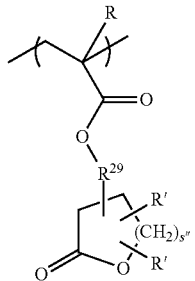

(a2-1)

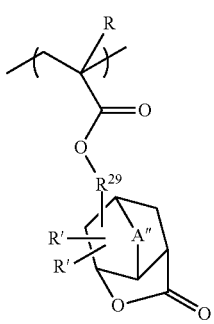

(a2-2)

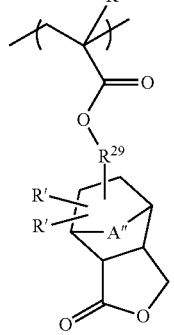

(a2-3)

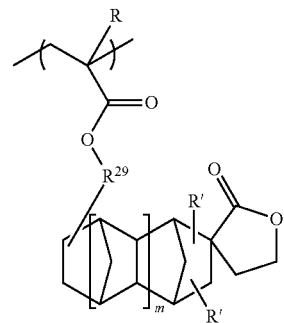

(a2-4)

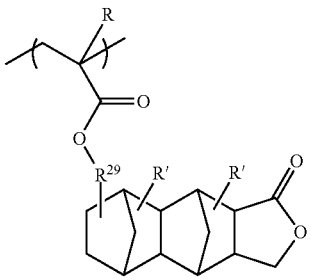

(a2-5)

In the formulas, R represents a hydrogen atom, an alkyl group of 1 to 5 carbon atoms or a halogenated alkyl group of 1 to 5 carbon atoms; each R' independently represents a hydrogen atom, an alkyl group of 1 to 5 carbon atoms, an alkoxy group of 1 to 5 carbon atoms or —COOR", wherein R" represents a hydrogen atom or an alkyl group; R$^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined above for R in the structural unit (a1).

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group.

In terms of industrial availability, R' is preferably a hydrogen atom.

The alkyl group for R" may be any of linear, branched or cyclic.

In those cases where R" represents a linear or branched alkyl group, the alkyl group preferably has 1 to 10 carbon atoms, and more preferably 1 to 5 carbon atoms.

In those cases where R" represents a cyclic alkyl group, the cyclic alkyl group preferably has 3 to 15 carbon atoms, more preferably 4 to 12 carbon atoms, and most preferably 5 to 10 carbon atoms. As examples of the cyclic alkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

As examples of A", the same groups as those described above for A' in general formula (3-1) can be given. A" is preferably an alkylene group of 1 to 5 carbon atoms, an oxygen atom (—O—) or a sulfur atom (—S—), and more preferably an alkylene group of 1 to 5 carbon atoms or —O—. As the alkylene group of 1 to 5 carbon atoms, a methylene group or a dimethylethylene group is preferable, and a methylene group is particularly desirable.

$R^{29}$ is the same as defined for $R^{29}$ in the aforementioned general formula (a2-0).

In formula (a2-1), s" is preferably 1 or 2.

Specific examples of structural units represented by general formulas (a2-1) to (a2-5) are shown below. In the formulas shown below, $R^\alpha$ represents a hydrogen atom, a methyl group or a trifluoromethyl group.

[Chemical Formula 38]

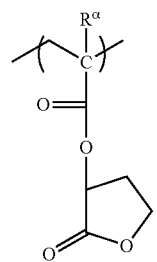
(a2-1-1)

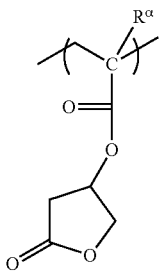
(a2-1-2)

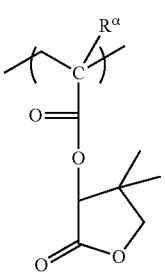
(a2-1-3)

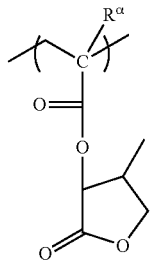
(a2-1-4)

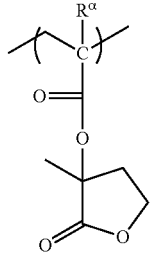
(a2-1-5)

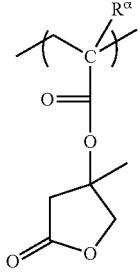
(a2-1-6)

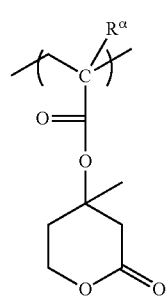
(a2-1-7)

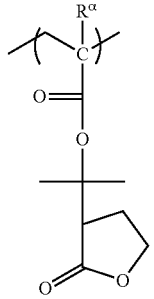
(a2-1-8)

(a2-1-9) 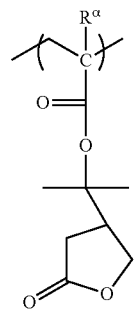
(a2-1-10) 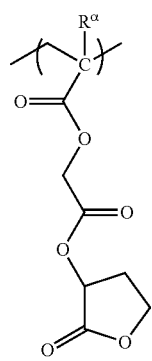
(a2-1-11) 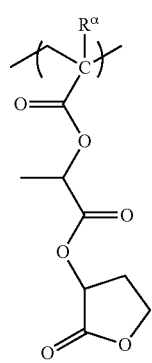
(a2-1-12) 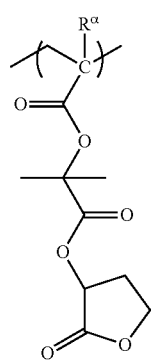
(a2-1-13) 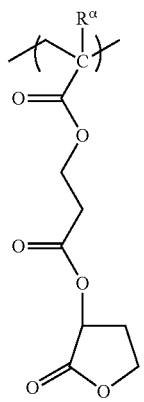
[Chemical Formula 39]
(a2-2-1) 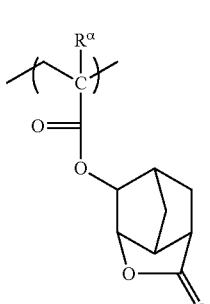
(a2-2-2) 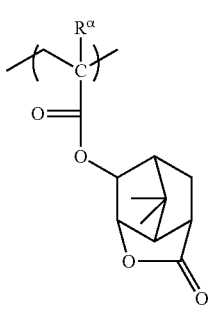
(a2-2-3) 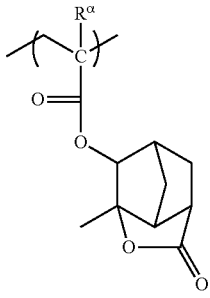
(a2-2-4) 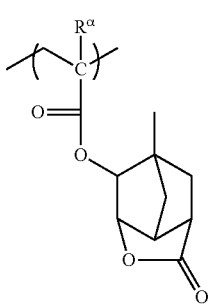

(a2-2-5)
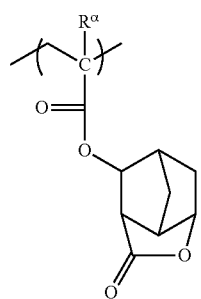
(a2-2-6)
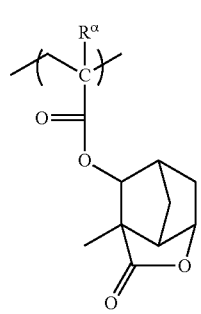
(a2-2-7)
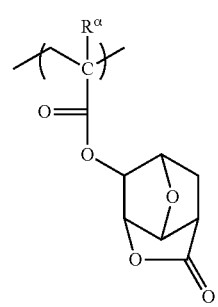
(a2-2-8)
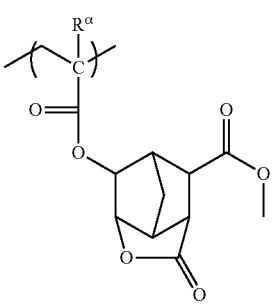
(a2-2-9)
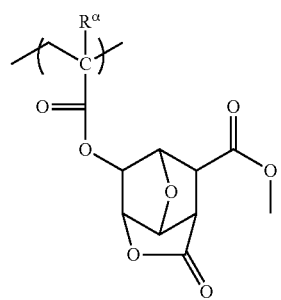
(a2-2-10)
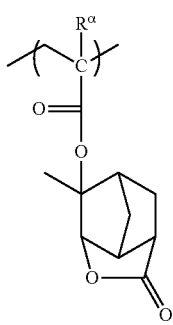
(a2-2-11)
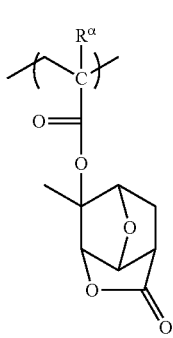
(a2-2-12)
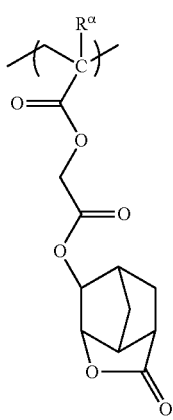
(a2-2-13)
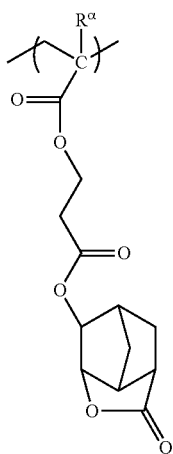

(a2-2-14)
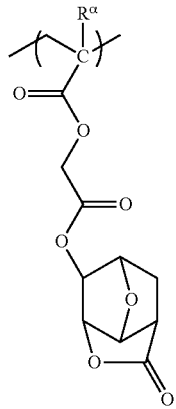
(a2-2-15)
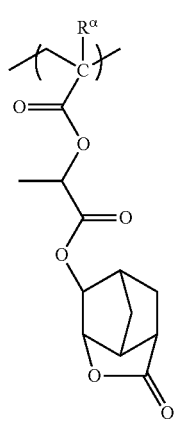
(a2-2-16)
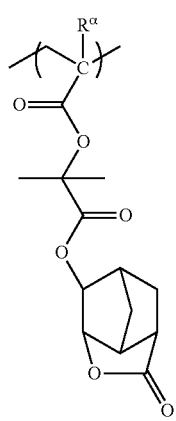
(a2-2-17)
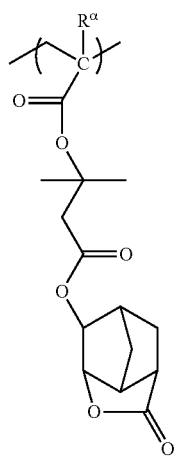
[Chemical Formula 40]
(a2-3-1)
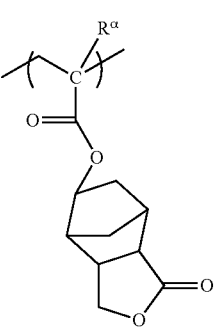
(a2-3-2)
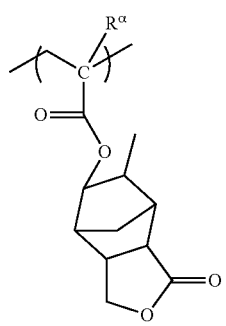
(a2-3-3)
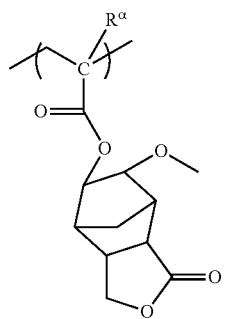

[Chemical Formula 41]

(a2-4-11)
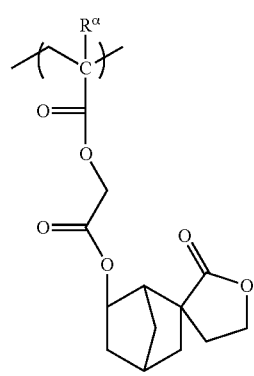
(a2-4-12)
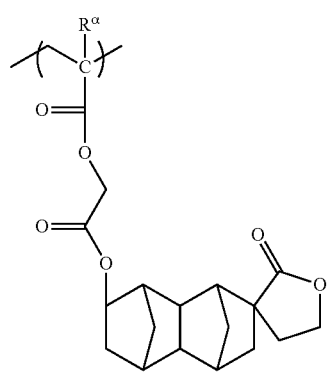
[Chemical Formula 42]
(a2-5-1)
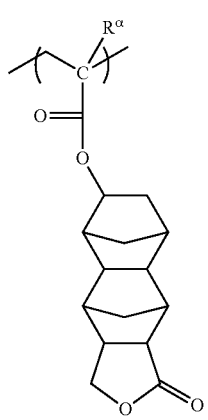
(a2-5-2)
(a2-5-3)
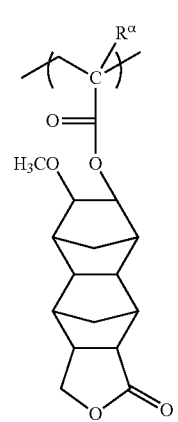
(a2-5-4)
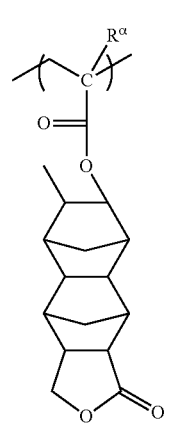
(a2-5-5)
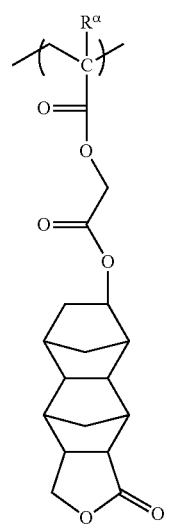

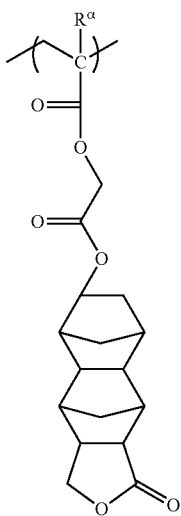

(a2-5-6)

As the structural unit (a2$^L$), at least one structural unit selected from the group consisting of structural units represented by the aforementioned general formulas (a2-1) to (a2-5) is preferable, at least one structural unit selected from the group consisting of structural units represented by the aforementioned general formulas (a2-1) to (a2-3) is more preferable, and at least one structural unit selected from the group consisting of structural units represented by the aforementioned general formulas (a2-1) and (a2-2) is particularly desirable.

Of these, it is particularly preferable to use at least one structural unit selected from the group consisting of structural units represented by the aforementioned formulas (a2-1-1), (a2-1-2), (a2-2-1), (a2-2-7), (a2-2-12), (a2-2-14), (a2-3-1) and (a2-3-5).

In the component (A1), as the structural unit (a2), one type of structural unit may be used alone, or two or more types of structural units may be used in combination. For example, as the structural unit (a2), a structural unit (a2$^S$) may be used alone, or a structural unit (a2$^L$) may be used alone, or a combination of these structural units may be used. Further, as the structural unit (a2$^S$) or the structural unit (a2$^L$), either a single type of structural unit may be used, or two or more types may be used in combination.

In the present invention, it is particularly desirable that the structural unit (a2) include at least the structural unit (a2$^L$), as the effects of the present invention are improved.

In the component (A1), the amount of the structural unit (a2) based on the combined total of all structural units constituting the component (A1) is preferably 1 to 80 mol %, more preferably 10 to 70 mol %, still more preferably 10 to 65 mol %, and most preferably 10 to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties, such as DOF and CDU, and pattern shape can be improved.

(Structural Unit (a3))

The structural unit (a3) is a structural unit containing a polar group-containing aliphatic hydrocarbon group and derived from an acrylate ester in which an atom other than a hydrogen atom or a substituent may be bonded to the carbon atom on the α-position.

When the component (A1) includes the structural unit (a3), the hydrophilicity of the component (A) is improved, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups).

These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that includes an aliphatic polycyclic group containing a hydroxyl group, cyano group, carboxyl group or a hydroxyalkyl group in which some of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 43]

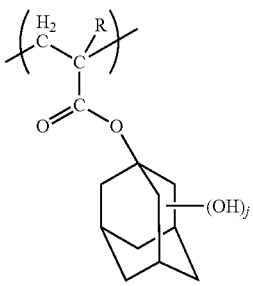

(a3-1)

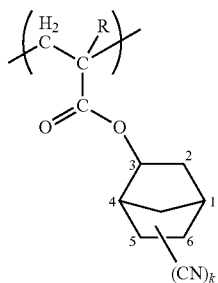

(a3-2)

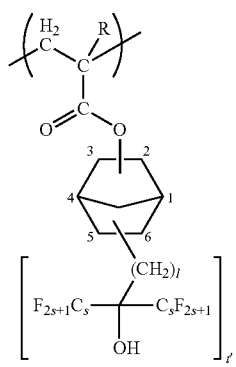

(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, in formula (a3-3), it is preferable that a 2-norbornyl group or 3-norbornyl group be bonded to the terminal of the carboxyl group of the acrylic acid. The fluorinated alkyl alcohol is preferably bonded to the 5th or 6th position of the norbornyl group.

As the structural unit (a3), one type of structural unit may be used alone, or two or more types of structural units may be used in combination.

The amount of the structural unit (a3) within the component (A1) based on the combined total of all structural units constituting the component (A1) is preferably 1 to 50 mol %, more preferably 3 to 45 mol %, and still more preferably 5 to 40 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

(Other Structural Units)

The component (A1) may also include a structural unit other than the above-mentioned structural units (a1) to (a3) (hereafter, referred to as "structural unit (a4)"), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), for example, structural units containing a non-acid dissociable, aliphatic polycyclic group and derived from an acrylate ester in which a hydrogen atom bonded to the carbon atom on the α-position may be substituted with a substituent, structural units derived from styrene monomers, hydroxystyrene monomers or vinylnaphthalene monomers, or the like are preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 44]

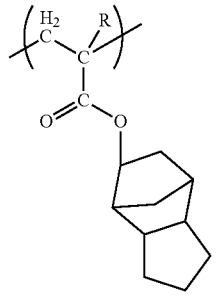

(a4-1)

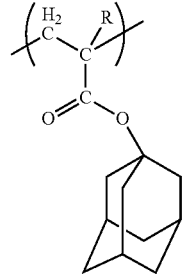

(a4-2)

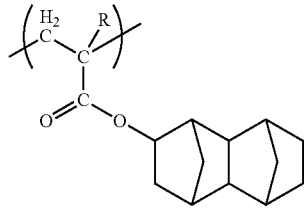

(a4-3)

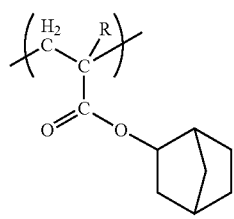

(a4-4)

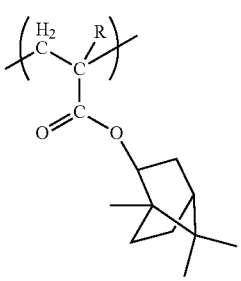

(a4-5)

In the formulas, R is the same as defined above.

As the structural unit (a4), one type of structural unit may be used alone, or two or more types of structural units may be used in combination.

When the structural unit (a4) is included in the component (A1), the amount of the structural unit (a4) based on the combined total of all structural units constituting the component (A1) is preferably 1 to 20 mol %, more preferably 1 to 15 mol %, and still more preferably 1 to 10 mol %.

The component (A1) is preferably a copolymer that further includes the structural unit (a1), in addition to the structural unit (a0).

Examples of such copolymers include a copolymer consisting of the structural units (a0) and (a1); a copolymer consisting of the structural units (a0), (a1) and (a3); a copolymer consisting of the structural units (a0), (a1) and (a2); and a copolymer consisting of the structural units (a0), (a1), (a2) and (a3).

In the present invention, it is particularly desirable that the component (A1) include a suitable combination of structural units represented by general formula (A1-11) to (A1-15) shown below. In general formulas shown below, R, $R^{29}$, s", $R^1$, A, $R^{11}$, $R^{12}$, h, j, $R^{15}$ and $R^{16}$ are the same as defined above, and the plurality of R and $R^{11}$ in the formulas may be the same or different from each other.

[Chemical Formula 45]

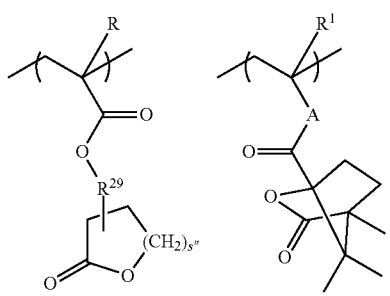

(A1-11)

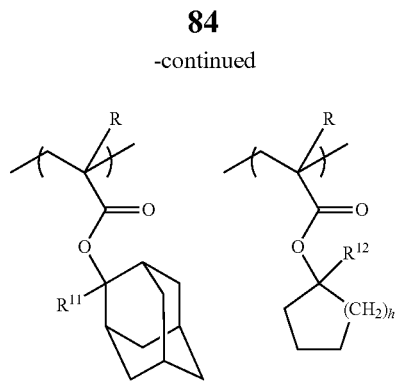

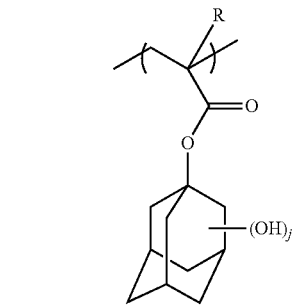

(A1-12)

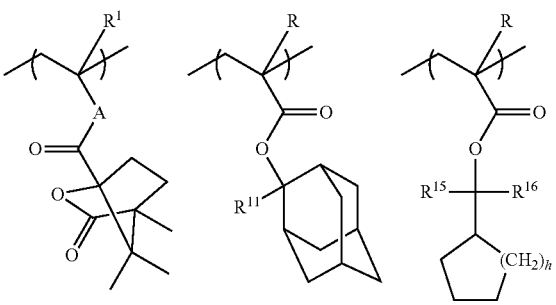

(A1-13)

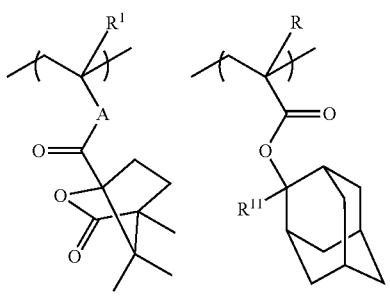

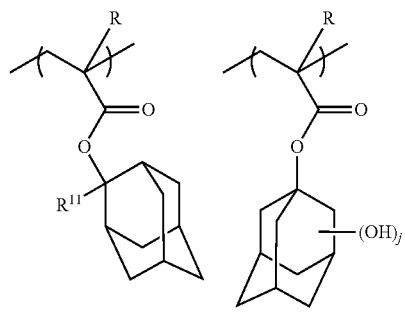

-continued

[Chemical Formula 46]

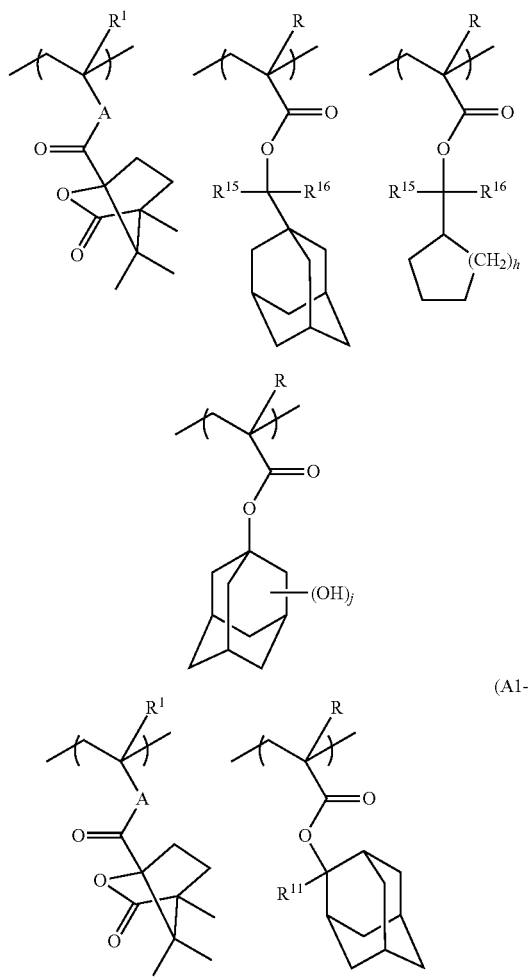

The weight average molecular weight (Mw) (the polystyrene equivalent value determined by gel permeation chromatography) of the component (A1) is not particularly limited, but is preferably within a range from 1,000 to 50,000, more preferably from 1,500 to 30,000, and most preferably from 2,500 to 20,000. Provided the weight average molecular weight is not more than the upper limit of the above-mentioned range, the component (A1) exhibits satisfactory solubility in a resist solvent when used as a resist, whereas provided the weight average molecular weight is at least as large as the lower limit of the above-mentioned range, the dry etching resistance and cross-sectional shape of the resist pattern can be improved.

Further, the dispersity (Mw/Mn) of the component (A1) is not particularly limited, but is preferably within a range from 1.0 to 5.0, more preferably from 1.0 to 3.0, and most preferably 1.2 to 2.5.

Here, Mn is the number average molecular weight.

In the component (A), as the component (A1), one type of component may be used alone, or two or more types may be used in combination.

In the component (A), the amount of the component (A1) based on the total weight of the component (A) is preferably 25% by weight or more, more preferably 50% by weight or more, still more preferably 75% by weight or more, and may be even 100% by weight. When the amount of the component (A1) is 25% by weight or more, various lithography properties are improved.

The positive resist composition of the present invention may contain, as the component (A), a base component (hereafter, referred to as "component (A2)") which exhibits increased solubility in an alkali developing solution under the action of acid, other than the aforementioned components (A0) and (A1).

As the component (A2), a low molecular weight compound that has a molecular weight of at least 500 but less than 2,500, contains a hydrophilic group, and also contains an acid dissociable group such as those listed above in connection with the component (A1) is preferred.

Specific examples include compounds containing a plurality of phenol skeletons in which a part of the hydrogen atoms within hydroxyl groups have been substituted with the aforementioned acid dissociable groups.

Preferred examples of the component (A2) include low molecular weight phenol compounds in which a portion of the hydroxyl group hydrogen atoms have been substituted with an aforementioned acid dissociable group. These types of compounds are known, for example, as sensitizers or heat resistance improvers for use in non-chemically amplified g-line or i-line resists, and any of these compounds may be used.

Specific examples of the low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers to hexamers of formalin condensation products of phenols such as phenol, m-cresol, p-cresol and xylenol. Needless to say, the low molecular weight phenol compound is not limited to these examples. Among these, in terms of achieving excellent resolution and LWR, a phenol compound having 2 to 6 triphenylmethane skeletons is particularly desirable.

Also, there are no particular limitations on the acid dissociable group, and suitable examples include the groups described above.

As the component (A2), one type may be used alone, or two or more types may be used in combination.

In the resist composition of the present invention, the component (A) may use either one type of component, or a combination of two or more components.

Of the various possibilities described above, the component (A) preferably includes the component (A1).

The amount of the component (A) within the resist composition of the present invention may be adjusted in accordance with factors such as the thickness of the resist film that is to be formed.

<Component (B)>

As the component (B), there is no particular limitation, and any of the known acid generators used in conventional chemically amplified resist compositions can be used. Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator, for example, a compound represented by general formula (b-1) or (b-2) shown below can be used.

[Chemical Formula 47]

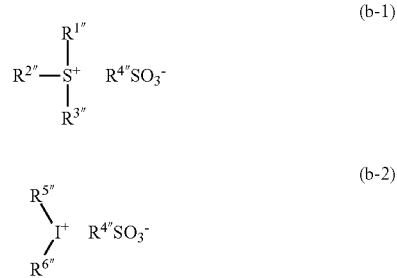

(b-1)

(b-2)

In the formulas above, $R^{1''}$ to $R^{3''}$, $R^{5''}$ and $R^{6''}$ each independently represents an aryl group or alkyl group, wherein two of $R^{1''}$ to $R^{3''}$ in formula (b-1) may be bonded to each other to form a ring with the sulfur atom in the formula; and $R^{4''}$ represents an alkyl group, a halogenated alkyl group, an aryl group or an alkenyl group which may have a substituent.

In formula (b-1), $R^{1''}$ to $R^{3''}$ each independently represents an aryl group or an alkyl group. In formula (b-1), two of $R^{1''}$ to $R^{3''}$ may be bonded to each other to form a ring with the sulfur atom in the formula.

Further, it is preferable that at least one group among $R^{1''}$ to $R^{3''}$ represent an aryl group. Among $R^{1''}$ to $R^{3''}$, two or more groups are preferably aryl groups, and it is particularly desirable that all of $R^{1''}$ to $R^{3''}$ are aryl groups.

The aryl group for $R^{1''}$ to $R^{3''}$ is not particularly limited. For example, an aryl group having 6 to 20 carbon atoms may be used, in which some or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and a naphthyl group.

The alkyl group with which hydrogen atoms of the aryl group may be substituted is preferably an alkyl group having 1 to 5 carbon atoms, and most preferably a methyl group, an ethyl group, a propyl group, an n-butyl group, or a tert-butyl group.

The alkoxy group with which hydrogen atoms of the aryl group may be substituted is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The halogen atom with which hydrogen atoms of the aryl group may be substituted is preferably a fluorine atom.

The alkyl group for $R^{1''}$ to $R^{3''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decyl group, and a methyl group is most preferable because it is excellent in resolution and can be synthesized at a low cost.

When two of $R^{1''}$ to $R^{3''}$ in formula (b-1) are bonded to each other to form a ring with the sulfur atom shown in the formula, it is preferable that the two of $R^{1''}$ to $R^{3''}$ form a 3- to 10-membered ring including the sulfur atom, and it is particularly desirable that the two of $R^{1''}$ to $R^{3''}$ form a 5- to 7-membered ring including the sulfur atom.

When two of $R^{1''}$ to $R^{3''}$ in formula (b-1) are bonded to each other to form a ring with the sulfur atom shown in the formula, the remaining one of $R^{1''}$ to $R^{3''}$ is preferably an aryl group. As examples of the aryl group, the same as the above-mentioned aryl groups for $R^{1''}$ to $R^{3''}$ can be given.

Preferred examples of the cation moiety for the compound represented by formula (b-1) include cation moieties represented by formulas (I-1-1) to (I-1-10) shown below. Among these, cation moieties having a triphenylmethane skeleton, such as those represented by any one of formulas (I-1-1) to (I-1-8) shown below are particularly desirable.

In formulas (I-1-9) and (I-1-10) shown below, each of $R^9$ and $R^{10}$ independently represents a phenyl group or naphthyl group which may have a substituent, an alkyl group of 1 to 5 carbon atoms, an alkoxy group or a hydroxyl group.

u represents an integer of 1 to 3, and is most preferably 1 or 2.

[Chemical Formula 48]

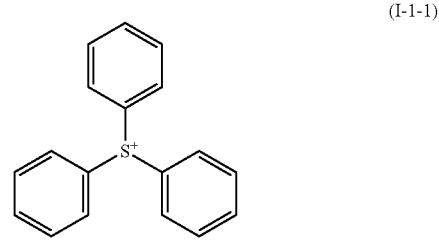

(I-1-1)

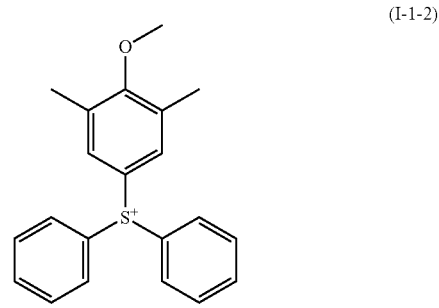

(I-1-2)

(I-1-3)
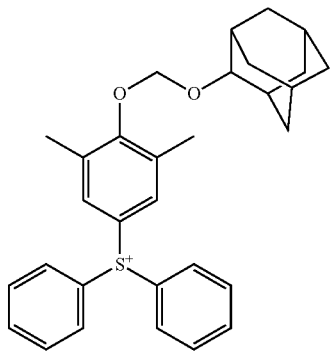

(I-1-4)
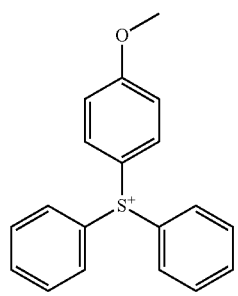

(I-1-5)
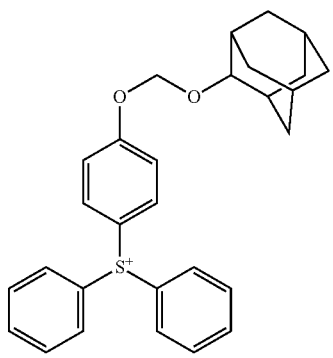

(I-1-6)
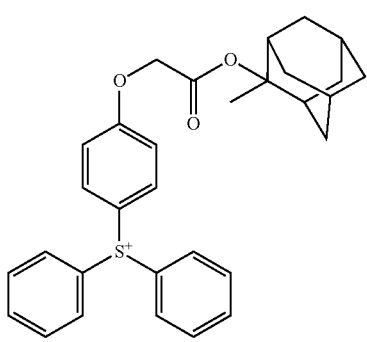

(I-1-7)
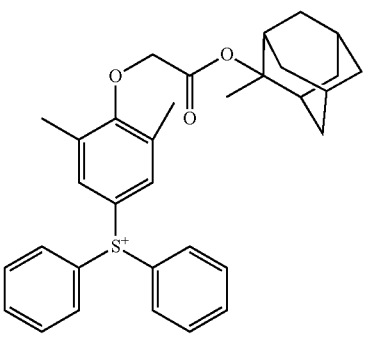

(I-1-8)
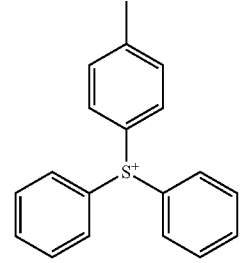

(I-1-9)
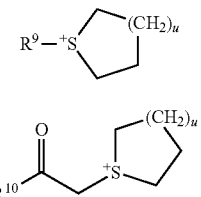

(I-1-10)

$R^{4''}$ represents an alkyl group, a halogenated alkyl group, an aryl group or an alkenyl group which may have a substituent.

The alkyl group for $R^{4''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As an example of the halogenated alkyl group for $R^{4''}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms based on the total number of halogen atoms and hydrogen atoms within the halogenated alkyl group (namely, the halogenation ratio (%)) is preferably within a range from 10 to 100%, more preferably from 50 to 100%, and most preferably 100%. A higher halogenation ratio is preferable because the acid strength increases.

The aryl group for $R^{4''}$ is preferably an aryl group of 6 to 20 carbon atoms.

The alkenyl group for $R^{4''}$ is preferably an alkenyl group of 2 to 10 carbon atoms.

With respect to $R^{4''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4''}$ may have one substituent, or two or more substituents.

Examples of the substituent include a halogen atom, a hetero atom, an alkyl group, and a group represented by the formula X-$Q^1$- [in the formula, $Q^1$ represents a divalent linking group containing an oxygen atom; and X represents a hydrocarbon group of 3 to 30 carbon atoms which may have a substituent].

Examples of halogen atoms and alkyl groups as substituents for $R^{4''}$ include the same halogen atoms and alkyl groups as those described above with respect to the halogenated alkyl group for $R^{4''}$.

Examples of the hetero atoms include an oxygen atom, a nitrogen atom, and a sulfur atom.

In the group represented by formula X-$Q^1$-, $Q^1$ represents a divalent linking group containing an oxygen atom.

$Q^1$ may also contain atoms other than the oxygen atom. Examples of atoms other than the oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an amide bond (—C(=O)—NH—), a carbonyl group (—C(=O)—) and a carbonate bond (—O—C(=O)—O—); and combinations of the aforementioned non-hydrocarbon, oxygen atom-containing linking groups with an alkylene group.

Specific examples of the combinations of the aforementioned non-hydrocarbon, oxygen atom-containing linking groups and an alkylene group include —$R^{91}$—O—, —$R^{92}$—O—C(=O)—, —C(=O)—O—$R^{93}$—O—C(=O)— (in the formulas, each of $R^{91}$ to $R^{93}$ independently represents an alkylene group).

The alkylene group for $R^{91}$ to $R^{93}$ is preferably a linear or branched alkylene group, and preferably has 1 to 12 carbon atoms, more preferably 1 to 5 carbon atoms, and most preferably 1 to 3 carbon atoms.

Specific examples of alkylene groups include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2$CH($CH_3$)$CH_2$—; a tetramethylene group [—$CH_2CH_2CH_2CH_2$—]; alkyltetramethylene groups such as —CH($CH_3$)$CH_2CH_2CH_2$— and —$CH_2$CH($CH_3$)$CH_2CH_2$—; and a pentamethylene group [—$CH_2CH_2CH_2CH_2CH_2$—].

$Q^1$ is preferably a divalent linking group containing an ester bond or ether bond, and more preferably a group represented by —$R^{91}$—O—, —$R^{92}$—O—C(=O)— or —C(=O)—O—$R^{93}$—O—C(=O)—.

In the group represented by the formula X-$Q^1$-, the hydrocarbon group for X may be either an aromatic hydrocarbon group or an aliphatic hydrocarbon group.

An aromatic hydrocarbon group is a hydrocarbon group having an aromatic ring. The aromatic hydrocarbon group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2 carbon atoms, and most preferably 1 carbon atom.

The aromatic hydrocarbon group may have a substituent. For example, some of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned hetero atom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, an ethoxy group, a n-propoxy group, an iso-propoxy group, a n-butoxy group or a tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for X may be either a saturated aliphatic hydrocarbon group, or an unsaturated aliphatic hydrocarbon group. Further, the aliphatic hydrocarbon group may be linear, branched or cyclic.

In the aliphatic hydrocarbon group for X, a part of the carbon atoms constituting the aliphatic hydrocarbon group may be substituted with a substituent group containing a hetero atom, or a part or all of the hydrogen atoms constituting the aliphatic hydrocarbon group may be substituted with a substituent group containing a hetero atom.

There are no particular limitations on this "hetero atom" within X, as long as it is an atom other than a carbon atom or a hydrogen atom. Examples of the hetero atom include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist solely of the hetero atom, or may be a group that also contains a group or atom other than the hetero atom.

Specific examples of the substituent group for substituting part of the carbon atoms include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, an ethoxy group, a n-propoxy group, an iso-propoxy group, a n-butoxy group or a tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Examples of the aforementioned halogenated alkyl group include a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15 carbon atoms, and most preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15 carbon atoms, and most preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5 carbon atoms, still more preferably 2 to 4 carbon atoms, and most preferably 3 carbon atoms. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms.

Examples of the aliphatic cyclic group include groups in which one or more hydrogen atoms have been removed from a monocycloalkane, and groups in which one or more hydrogen atoms have been removed from a polycycloalkane such as a bicycloalkane, tricycloalkane or tetracycloalkane. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L6) and (S1) to (S4) shown below.

[Chemical Formula 49]

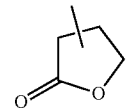

(L1)

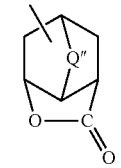

(L2)

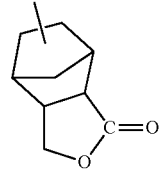

(L3)

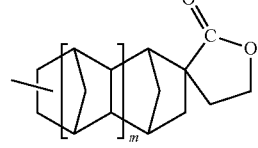

(L4)

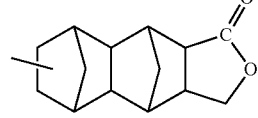

(L5)

(L6)

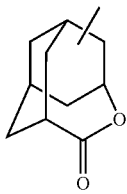

(S1)

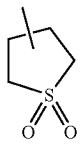

(S2)

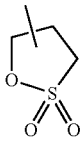

(S3)

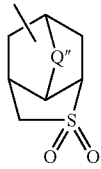

(S4)

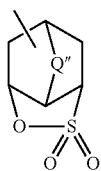

In the formulas, Q″ represents an alkylene group of 1 to 5 carbon atoms, —O—, —S—, —O—$R^{94}$— or —S—$R^{95}$— (wherein each of $R^{94}$ and $R^{95}$ independently represents an alkylene group of 1 to 5 carbon atoms); and m represents an integer of 0 or 1.

As the alkylene group for Q″, $R^{94}$ and $R^{95}$, the same alkylene groups as those described above for $R^{91}$ to $R^{93}$ can be used.

In these aliphatic cyclic groups, part of the hydrogen atoms bonded to the carbon atoms constituting the ring structure may be substituted with a substituent. Examples of the substituent include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

In the present invention, X is preferably a cyclic group which may have a substituent. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by formulas (L2) to (L6), (S3) and (S4) are preferable.

In the present invention, $R^{4″}$ preferably has X-$Q^1$- as a substituent. In such a case, $R^{4″}$ is preferably a group represented by the formula X-$Q^1$-$Y^1$— [in the formula, $Q^1$ and X are the same as defined above; and $Y^1$ represents an alkylene group of 1 to 4 carbon atoms which may have a substituent, or a fluorinated alkylene group of 1 to 4 carbon atoms which may have a substituent].

In the group represented by the formula X-$Q^1$-$Y^1$—, as the alkylene group for $Y^1$, the same alkylene group as those described above for $Q^1$ in which the number of carbon atoms is 1 to 4 can be used.

As the fluorinated alkylene group for $Y^1$, the aforementioned alkylene group in which a part or all of the hydrogen atoms in the alkylene group have been substituted with fluorine atoms can be used.

Specific examples of $Y^1$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

$Y^1$ is preferably a fluorinated alkylene group, and particularly preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The expression that the alkylene group or fluorinated alkylene group "may have a substituent" means that some or all of the hydrogen atoms or fluorine atoms in the alkylene group or fluorinated alkylene group may be substituted, either with atoms other than hydrogen atoms and fluorine atoms, or with groups.

Examples of substituents which the alkylene group or fluorinated alkylene group may have include an alkyl group of 1 to 4 carbon atoms, an alkoxy group of 1 to 4 carbon atoms, and a hydroxyl group.

In formula (b-2), $R^{5″}$ and $R^{6″}$ each independently represents an aryl group or an alkyl group. At least one of $R^{5″}$ and $R^{6″}$ represents an aryl group. It is preferable that both of $R^{5″}$ and $R^{6″}$ represent an aryl group.

As the aryl group for $R^{5''}$ and $R^{6''}$, the same as the aryl groups for $R^{1''}$ to $R^{3''}$ can be used.

As the alkyl group for $R^{5''}$ and $R^{6''}$, the same as the alkyl groups for $R^{1''}$ to $R^{3''}$ can be used.

It is particularly desirable that both of $R^{5''}$ and $R^{6''}$ represents a phenyl group.

As $R^{4''}$ in formula (b-2), the same groups as those mentioned above for $R^{4''}$ in formula (b-1) can be used.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts has been replaced by either an alkylsulfonate such as methanesulfonate, n-propanesulfonate, n-butanesulfonate, n-octanesulfonate, 1-adamantanesulfonate, 2-norbornanesulfonate and d-camphor-10-sulfonate; or an aromatic sulfonate such as benzenesulfonate, perfluorobenzenesulfonate or p-toluenesulfonate.

Furthermore, onium salts in which the anion moiety of these onium salts has been replaced by an anion moiety represented by any one of formulas (b1) to (b8) shown below can also be used.

[Chemical Formula 50]

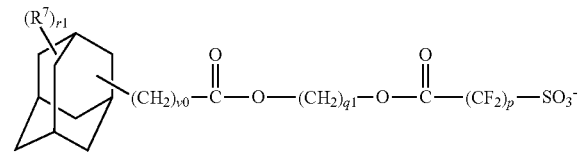
(b1)

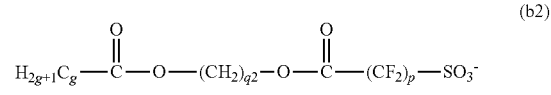
(b2)

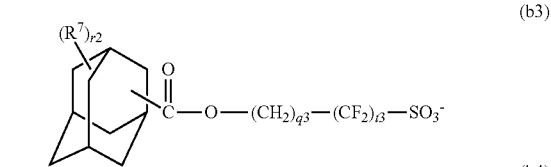
(b3)

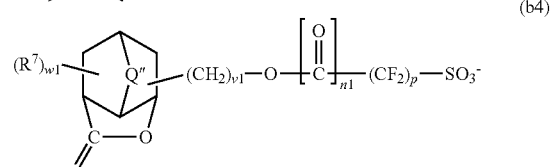
(b4)

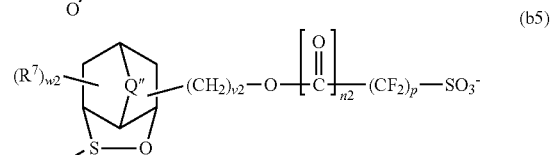
(b5)

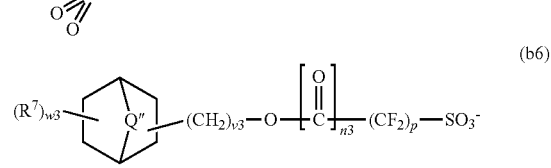
(b6)

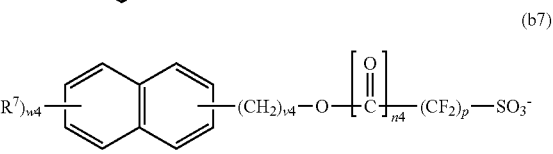
(b7)

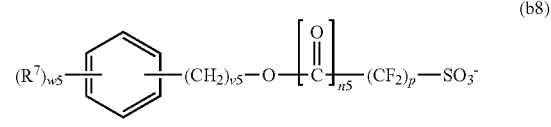
(b8)

In the formulas, p represents an integer of 1 to 3; each of q1 and q2 independently represents an integer of 1 to 5; q3 represents an integer of 1 to 12; t3 represents an integer of 1 to 3; each of r1 and r2 independently represents an integer of 0 to 3; g represents an integer of 1 to 20; $R^7$ represents a substituent; each of n1 to n5 independently represents 0 or 1; each of v0 to v5 independently represents an integer of 0 to 3; each of w1 to w5 independently represents an integer of 0 to 3; and Q" is the same as defined above.

As the substituent for $R^7$, the same groups as those which the aforementioned aliphatic hydrocarbon group or aromatic hydrocarbon group for X may have as a substituent can be used.

If there are two or more of the $R^7$ group, as indicated by the values r1, r2, and w1 to w5, then the two or more of the $R^7$ groups may be the same or different from each other.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may be used.

[Chemical Formula 51]

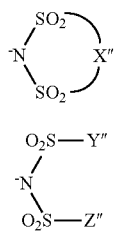

(b-3)

(b-4)

In the formulas, X" represents an alkylene group of 2 to 6 carbon atoms in which at least one hydrogen atom has been substituted with a fluorine atom; and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved. The amount of fluorine atoms within the alkylene group or alkyl group, i.e., fluorination ratio, is preferably from 70 to 100%, more preferably from 90 to 100%, and it is particularly desirable that the alkylene group or alkyl group be a perfluoroalkylene or perfluoroalkyl group in which all hydrogen atoms are substituted with fluorine atoms.

Furthermore, as the onium salt-based acid generator, a sulfonium salt having a cation moiety represented by general formula (b-5) or (b-6) shown below may also be used.

[Chemical Formula 52]

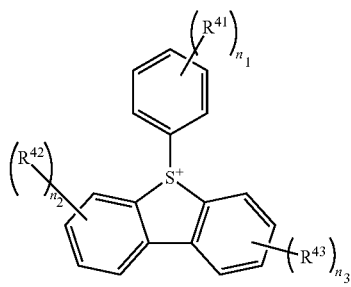

(b-5)

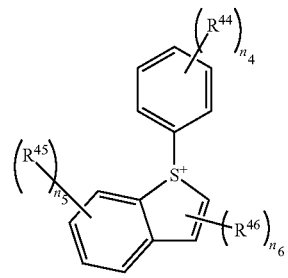

(b-6)

In the formulas, each of $R^{41}$ to $R^{46}$ independently represents an alkyl group, an acetyl group, an alkoxy group, a carboxy group, a hydroxyl group or a hydroxyalkyl group; each of $n_1$ to $n_5$ independently represents an integer of 0 to 3; and $n_6$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, a n-butyl group or a tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

When the subscripts $n_1$ to $n_6$ of $R^{41}$ to $R^{46}$ represent an integer of 2 or more, the plurality of $R^{41}$ to $R^{46}$ may be the same or different.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.
$n_5$ is preferably 0 or 1, and more preferably 0.
$n_6$ is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used. Examples of such anion moieties include fluorinated alkylsulfonic acid ions such as anion moieties ($R^{4''}SO_3^-$) for onium salt-based acid generators represented by general formula (b-1) or (b-2) shown above; and anion moieties represented by general formula (b-3) or (b-4) shown above.

In the present description, an oxime sulfonate-based acid generator is a compound having at least one group represented by general formula (B-1) shown below, and has a feature of generating acid by irradiation. Such oxime sulfonate-based acid generators are widely used for a chemically amplified resist composition, and can be appropriately selected.

[Chemical Formula 53]

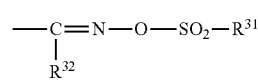

(B-1)

In formula (B-1), each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for R31, a linear, branched, or cyclic alkyl group or an aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression that the alkyl group or aryl group "may have a substituent" means that some or all of the hydrogen atoms of the alkyl group or aryl group may be substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, an aryl group, or a cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 54]

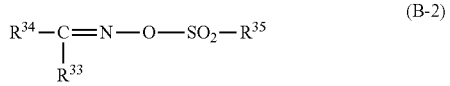

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 55]

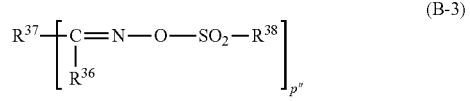

(B-3)

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms thereof fluorinated, more preferably 70% or more fluorinated, and still more preferably 90% or more fluorinated. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 86) may be preferably used.

Furthermore, as preferable examples, the following can be used.

[Chemical Formula 56]

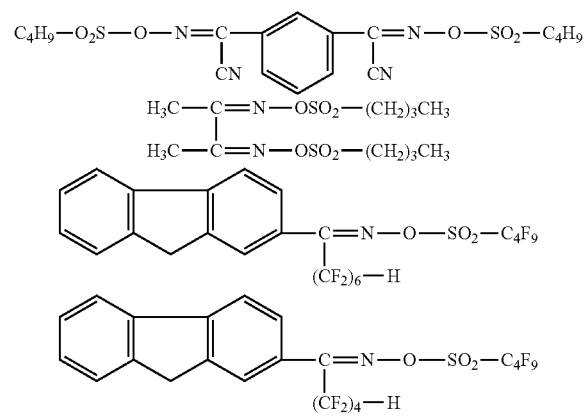

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may also be used favorably.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis (phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B), one type of acid generator may be used alone, or two or more types of acid generators may be used in combination.

In the present invention, the component (B) is preferably an onium salt-based acid generator having a fluorinated alkylsulfonic acid ion as the anion moiety. Further, it is also preferable to use an onium salt-based acid generator having a fluorinated alkylsulfonic acid ion as the anion moiety in combination with an onium salt-based acid generator containing a weak acid anion such as d-camphor-10-sulfonate.

In the positive resist composition of the present invention, the amount of the component (B) relative to 100 parts by weight of the component (A) is preferably 0.5 to 60 parts by weight, and more preferably 1 to 50 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>

[Component (D)]

It is preferable that the resist composition of the present invention further includes a nitrogen-containing organic compound (D) (hereafter referred to as the component (D)) as an optional component.

As the component (D), there is no particular limitation as long as it functions as an acid diffusion control agent, i.e., a quencher which traps the acid generated from the component (B) upon exposure. A multitude of these components (D) have already been proposed, and any of these known compounds may be used. Among these, an aliphatic amine is preferable, and a secondary aliphatic amine or tertiary aliphatic amine is particularly desirable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (that is, alkylamines or alkyl alcohol amines), and cyclic amines.

Specific examples of the alkylamines or alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are more preferable, and tri-n-pentylamine or tri-n-octylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferred.

Further, as the component (D), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonyl pyrrolidine.

As the component (D), one type may be used alone, or two or more types may be used in combination.

The component (D) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added as an optional component.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid, and among these, phosphonic acid is particularly desirable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phenylphosphinic acid and phosphinic acid esters.

As the component (E), one type may be used alone, or two or more types may be used in combination.

As the component (E), an organic carboxylic acid is preferred, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition according to the present invention can be prepared by dissolving the components added to the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples of the component (S) include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

The component (S) can be used individually, or as a mixed solvent containing two or more different solvents.

Among these, γ-butyrolactone, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably in the range of 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Furthermore, as the component (S), a mixed solvent of PGMEA, PGME and cyclohexanone is also preferable. In this case, it is preferable that the mixing ratio in terms of the weight ratio be PGMEA:PGME: cyclohexanone=(from 35 to 55):(from 25: to 45):(from 10 to 30).

The amount of the component (S) used is not particularly limited, and is appropriately adjusted to a concentration that enables application of a coating solution to a substrate, depending on the thickness of the coating film. In general, the component (S) is used in an amount that yields a solid content for the resist composition that is within the range from 0.5 to 20% by weight, and preferably from 1 to 15% by weight.

Dissolving of the components to be added to the resist composition in the component (S) can be conducted, for example, by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, or a membrane filter or the like.

As described above, the component (A) used in the resist composition of the present invention is a novel component essentially unknown in the art.

In the resist composition of the present invention, by using the component (A) that includes the structural unit (a0), lithography properties such as the LWR and resolution are improved.

Although the reason why these effects can be achieved has not been elucidated yet, it is thought that by including a skeleton derived from camphanic acid that exhibits moderate polarity within the structural unit (a0), the solubility of the resist composition in an organic solvent is increased, and also the swelling of the coating film is reduced, thereby improving the lithography properties.

<<Method of Forming a Resist Pattern>>

The method of forming a resist pattern according to the second aspect of the present invention includes: applying the aforementioned resist composition according to the first aspect of the present invention to a substrate to form a resist film on the substrate; conducting exposure of the resist film; and developing the resist film to form a resist pattern.

More specifically, the method of forming a resist pattern according to the present invention can be performed, for example, as follows.

Firstly, the aforementioned resist composition is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an electron beam exposure apparatus or the like, the resist film is selectively exposed to an electron beam (EB) through a desired mask pattern, followed by post exposure bake (PEB) under temperature conditions of 80 to 150° C. for 40 to 120 seconds, preferably 60 to 90 seconds. Subsequently, the resist film is subjected to a developing treatment.

In the case of alkali developing process, an alkali developing treatment is conducted using an alkali developing solution such as a 0.1 to 10% by weight aqueous solution of tetramethylammonium hydroxide (TMAH).

Further, in the case of solvent developing process, a developing treatment is conducted using an organic solvent. This organic solvent may be any organic solvent which can dissolve the component (A) (namely, the component (A) prior to exposure), and can be selected appropriately from amongst the known organic solvents. More specifically, polar solvents such as ketone-based solvents, ester-based solvents, alcohol-based solvents, amide-based solvents or ether-based solvents; and hydrocarbon-based solvents can be used, and among these, ester-based solvents are particularly desirable. As the ester-based solvent, butyl acetate is preferred.

After the developing treatment, a rinsing treatment is preferably conducted. In the case of alkali developing process, following the process, a water rinse using pure water is preferred. In the case of solvent developing process, following the process, a rinsing liquid containing the organic solvents listed above is preferably used.

Thereafter, drying is carried out. If desired, a bake treatment (post bake) may be conducted following the above developing treatment. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays.

The resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (an immersion medium) that has a larger refractive index than the refractive index of air.

More specifically, in immersion lithography, the region between the resist film formed in the above-described manner and lens at the lowermost portion of the exposure apparatus is filled with a solvent (an immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound includes perfluorotributylamine (boiling point 174° C.).

As the immersion medium, water is preferable in terms of cost, safety, environment and versatility.

<<Polymeric Compound>>

A polymeric compound according to the third aspect of the present invention is a polymeric compound including the structural unit (a0) represented by general formula (a0) shown below.

The same explanations as those provided for the component (A0) in the resist composition according to the first aspect can be applied to the polymeric compound of the present invention.

[Chemical Formula 57]

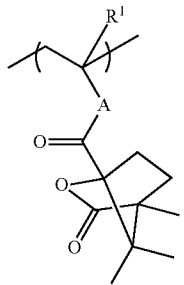

(a0)

In the formula, A represents a divalent linking group; and $R^1$ represents a hydrogen atom or a hydrocarbon group of 1 to 6 carbon atoms which may have a substituent.

<<Compound>>

A compound according to the fourth aspect of the present invention is a compound represented by general formula (I) shown below (hereafter, this compound is referred to as "compound (I)").

In formula (I), $R^1$ and A are the same as defined above for $R^1$ and A in formula (a0).

The compound (I) is useful as a monomer to be used in the production of the aforementioned component (A0).

[Chemical Formula 58]

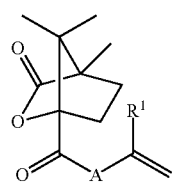

(I)

In the formula, A represents a divalent linking group; and $R^1$ represents a hydrogen atom or a hydrocarbon group of 1 to 6 carbon atoms which may have a substituent.

(Production Method of Compound)

The method of producing the compound (I) of the present invention is not particularly limited. However, for example, in those cases where the terminal of A which is bonded to the skeleton derived from camphanic acid is represented by —O—, the compound (I) can be produced by reacting a compound (i-1) represented by formula (i-1) shown below with a compound (i-2) represented by formula (i-2) shown below.

[Chemical Formula 59]

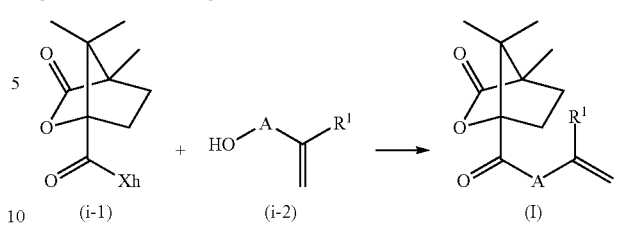

In the formulas, $R^1$ and A are the same as defined above for $R^1$ and A in general formula (a0), and Xh represents a halogen atom.

In the above formula (i-1), Xh represents a halogen atom, and a fluorine atom, a chlorine atom, a bromine atom, an iodine atom or the like is preferred.

In the above formula (i-2), $R^1$ and A are the same as defined above.

There are no particular limitations on the method used for reacting the compound (i-1) and the compound (i-2), and, for example, the method can be conducted as follows. The compound (i-2) is dissolved in an appropriate organic solvent, and the resultant is then stirred in the presence of an appropriate base. Then, the compound (i-1) is added thereto, and following stirring, the reaction mixture is washed and recovered.

As the compound (i-1) and the compound (i-2), commercially available compounds may be used, or the compounds may be synthesized.

In the above reaction, chlorinated hydrocarbon solvents such as dichloromethane are preferred as the organic solvent, and the amount thereof used in the reaction is preferably from 0.5 to 100 parts by weight, and more preferably from 0.5 to 20 parts by weight, relative to the compound (i-1). As a solvent, one type of solvent may be used alone, or two or more types of solvents may be used in combination.

Examples of the base include potassium carbonate, tertiary amines such as triethylamine, and aromatic amines such as pyridine. These bases may be used individually, or two or more types thereof may be used in combination. The amount of the base used may be a catalyst amount, and is typically about 0.01 to about 10 moles, per 1 mole of the compound (i-1).

The reaction time in the above reaction varies, depending on the reactivity of the compound (i-1) and the compound (i-2), the reaction temperature, and the like, but in general, the reaction time is preferably 1 to 80 hours, and more preferably 2 to 60 hours.

The reaction temperature in the above reaction is preferably 0 to 200° C., and more preferably 0 to about 150° C.

In general, the amount of the compound (i-2) used in the above reaction is preferably about 0.5 to 5 moles, and more preferably about 0.8 to 4 moles, per 1 mole of the compound (i-1).

After the reaction, the compound (I) within the reaction liquid may be separated and purified. The separation and purification can be conducted by a conventional method. For example, any one of concentration, solvent extraction, distillation, crystallization, recrystallization, chromatography, and the like can be used alone, or two or more of these methods may be used in combination.

The structure of the compound according to the present invention which is obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

EXAMPLES

As follows is a more detailed description of the present invention based on a series of examples, although the scope of the present invention is in no way limited by these examples.

In the NMR analysis in the present examples, the internal standard for $^1$H-NMR was tetramethylsilane (TMS), and the internal standard for $^{19}$F-NMR was hexafluorobenzene (provided that the peak of hexafluorobenzene was regarded as −160 ppm).

Synthesis Example 1

Synthesis of Compound (2)

Under a nitrogen atmosphere, 2-hydroxyethylmethacrylate (10.3 g) and dichloromethane (41 g) were added to a three-necked flask and cooled to 5° C.

Subsequently, triethylamine (8.0 g) was dropwise added thereto, and then a dichloromethane solution containing (−)-camphanic chloride (16.3 g) was dropwise added thereto over 1 hour. Then, the resultant was elevated to room temperature and stirred for 2 hours. Then, a 1% aqueous hydrochloric acid solution (85 g) was added to the reaction solution, and the resulting mixture was stirred for 10 minutes, followed by liquid separation.

The obtained dichloromethane layer was washed three times with pure water (85 g), and the resulting solution was dropwise added to n-hexane (410 g), thereby yielding 21 g of an objective product in the form of a white powder.

The obtained compound was analyzed by NMR, and the structure thereof was identified based on the results shown below.

$^1$H-NMR (400 MHz, DMSO-d6): δ (ppm)=0.82 (s, 3H, $CH_3$), 0.992 (s, 3H, $CH_3$), 1.01 (s, 3H, $CH_3$), 1.53-1.59 (m, 1H, Camphane), 1.88-2.02 (m, 5H, $CH_3$+Camphane), 2.33-2.40 (m, 1H, Camphane), 4.36-4.51 (m, 4H, $CH_2CH_2$), 5.71-5.72 (m, 1H, C=CH), 6.03 (brs, 1H, C=CH).

From the analytical results shown above, it was confirmed that the obtained compound (2) had a structure shown below.

[Chemical Formula 60]

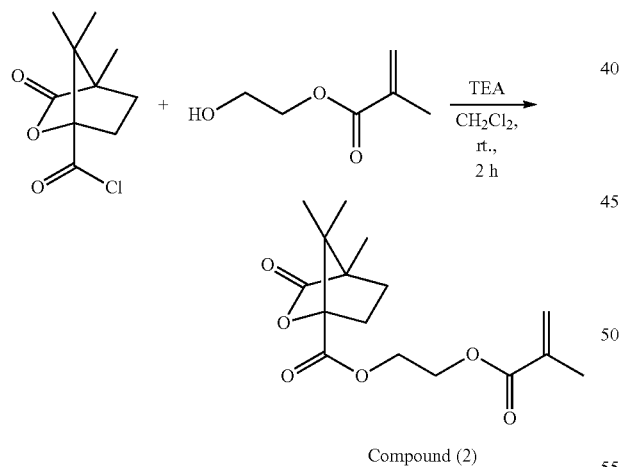

Compound (2)

Synthesis Example 2

Synthesis of Polymeric Compound (A)-1

In a separable flask equipped with a thermometer, a reflux tube and a nitrogen feeding pipe, 5.00 g (29.38 mmol) of a compound (1) shown below, 5.26 g (16.93 mmol) of the above compound (2), 7.45 g (28.39 mmol) of a compound (3) shown below, 2.35 g (13.95 mmol) of a compound (4) shown below and 2.59 g (10.96 mmol) of a compound (5) shown below were dissolved in 29.09 g of methyl ethyl ketone (MEK). Then, 4.98 mmol of dimethyl 2,2'-azobis(isobutyrate) (product name: V-601, Wako Pure Chemical Industries, Ltd.) as a polymerization initiator was added and dissolved in the resulting solution.

The resultant was dropwise added to 15.78 g of MEK heated to 80° C. in a nitrogen atmosphere over 3 hours. Following the dropwise addition, the resulting reaction solution was heated while stirring for 2 hours, and then cooled to room temperature.

The obtained reaction polymer solution was dropwise added to an excess amount of n-heptane to precipitate a polymer. Thereafter, the precipitated white powder was separated by filtration, followed by washing with methanol and drying, thereby obtaining 11.73 g of a polymeric compound (A)-1 as an objective compound.

With respect to this polymeric compound (A)-1, the weight average molecular weight (Mw) and the dispersity (Mw/Mn) were determined by the polystyrene equivalent value as measured by gel permeation chromatography (GPC). As a result, it was found that the weight average molecular weight was 8,200, and the dispersity was 1.66. Further, as a result of an analysis by carbon 13 nuclear magnetic resonance spectroscopy (600 MHz, $^{13}$C-NMR), it was found that the composition of the copolymer (ratio (molar ratio) of the respective structural units within the structural formula) was l/m/n/o/p=34.2/18.9/18.9/15.4/12.6.

From the analytical results shown above, it was confirmed that the obtained polymeric compound (A)-1 had a structure shown below.

[Chemical Formula 61]

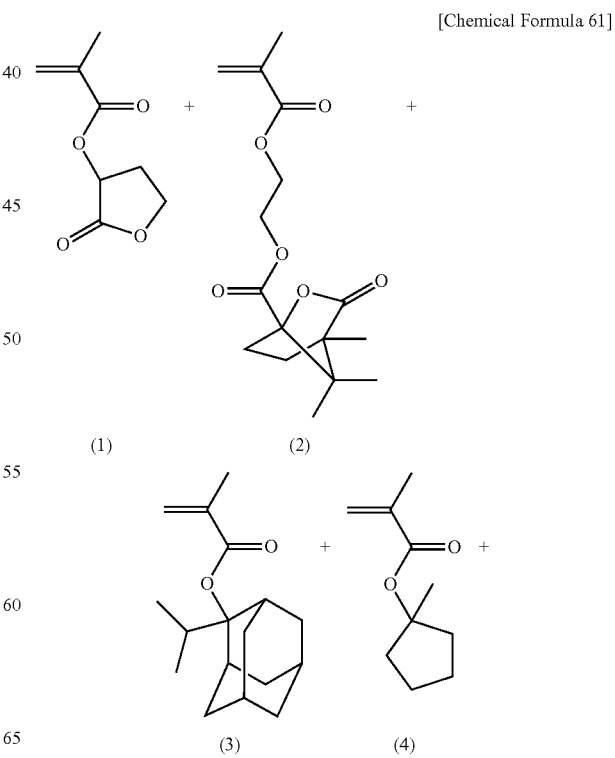

(1)　(2)

(3)　(4)

-continued

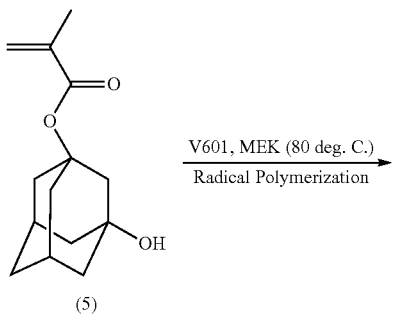

(5)

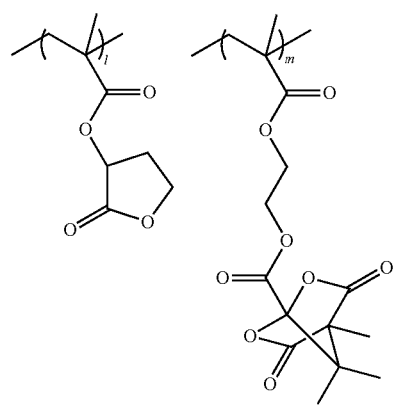

(A)-1

Example 1

Comparative Example 1

[Evaluation of Resin Solubility]

Each of the organic solvents listed in Table 1 was added to the polymeric compound (A)-1 (Example 1) or to a polymeric compound (A)-A (Comparative Example 1) shown below, and the resulting mixture was stirred at 23° C. for one hour so as to yield a solid content of 1% or 20%. Thereafter, the degree of dissolution of resins within the respective organic solvents was evaluated by visual inspection in accordance with the following evaluation criteria. The results are shown in Table 1.

A: readily soluble
B: soluble
C: insoluble

TABLE 1

|  | Comparative Example 1 (A)-A | | Example 1 (A)-1 | |
| --- | --- | --- | --- | --- |
| Solvent | 1% | 20% | 1% | 20% |
| PGME | — | B | — | A |
| PGMEA | C | C | — | A |
| Cyclohexanone | — | A | — | A |
| Butyl acetate | C | C | — | A |

[Chemical Formula 62]

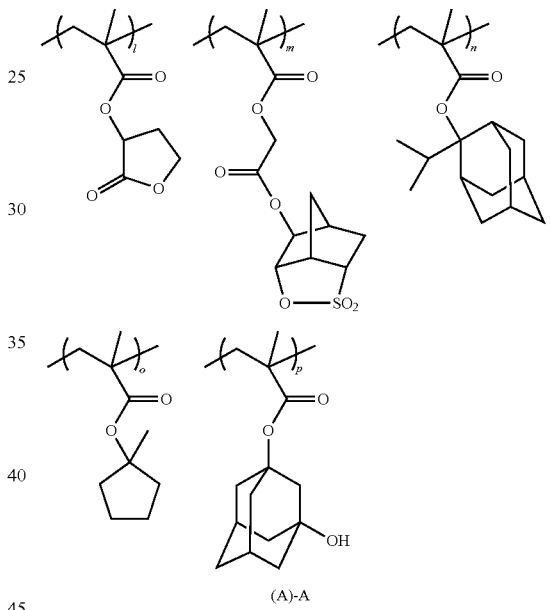

(A)-A

[Mw = 7,900, Mw/Mn = 1.57, l/m/n/o/p (molar ratio) = 34.7/21.7/16.3/14.8/12.5]

As seen from the results shown in Table 1, it was confirmed that the resist composition of Example 1 exhibited superior solubility in organic solvents, as compared to the resist composition of Comparative Example 1.

Examples 2 to 6

Comparative Examples 2 to 8

The components shown in Table 2 were mixed together and dissolved to obtain positive resist compositions.

TABLE 2

|  | Component (A) | Component (B) | | Component (D) | Component (E) | Component (S) |
| --- | --- | --- | --- | --- | --- | --- |
| Ex. 2 | (A)-1 | (B)-1 | (B)-2 | (D)-1 | (E)-1 | (S)-1 |
|  | [100] | [8.81] | [3.11] | [0.38] | [0.47] | [2,700] |
| Ex. 3 | (A)-2 | (B)-1 | (B)-2 | (D)-1 | (E)-1 | (S)-1 |
|  | [100] | [8.81] | [3.11] | [0.38] | [0.47] | [2,700] |
| Ex. 4 | (A)-3 | (B)-1 | (B)-2 | (D)-1 | (E)-1 | (S)-1 |
|  | [100] | [8.81] | [3.11] | [0.38] | [0.47] | [2,700] |
| Ex. 5 | (A)-4 | (B)-1 | (B)-2 | (D)-1 | (E)-1 | (S)-1 |

TABLE 2-continued

|  | Component (A) | Component (B) | Component (D) | Component (E) | Component (S) |
|---|---|---|---|---|---|
|  | [100] | [8.81] [3.11] | [0.38] | [0.47] | [2,700] |
| Ex. 6 | (A)-5 | (B)-1 (B)-2 | (D)-1 | (E)-1 | (S)-1 |
|  | [100] | [8.81] [3.11] | [0.38] | [0.47] | [2,700] |
| Comp. Ex. 2 | (A)-A | (B)-1 (B)-2 | (D)-1 | (E)-1 | (S)-1 |
|  | [100] | [8.81] [3.11] | [0.38] | [0.47] | [2,700] |
| Comp. Ex. 3 | (A)-B | (B)-1 (B)-2 | (D)-1 | (E)-1 | (S)-1 |
|  | [100] | [8.81] [3.11] | [0.38] | [0.47] | [2,700] |
| Comp. Ex. 4 | (A)-C | (B)-1 (B)-2 | (D)-1 | (E)-1 | (S)-1 |
|  | [100] | [8.81] [3.11] | [0.38] | [0.47] | [2,700] |
| Comp. Ex. 5 | (A)-D | (B)-1 (B)-2 | (D)-1 | (E)-1 | (S)-1 |
|  | [100] | [8.81] [3.11] | [0.38] | [0.47] | [2,700] |
| Comp. Ex. 6 | (A)-E | (B)-1 (B)-2 | (D)-1 | (E)-1 | (S)-1 |
|  | [100] | [8.81] [3.11] | [0.38] | [0.47] | [2,700] |
| Comp. Ex. 7 | (A)-F | (B)-1 (B)-2 | (D)-1 | (E)-1 | (S)-1 |
|  | [100] | [8.81] [3.11] | [0.38] | [0.47] | [2,700] |
| Comp. Ex. 8 | (A)-G | (B)-1 (B)-2 | (D)-1 | (E)-1 | (S)-1 |
|  | [100] | [8.81] [3.11] | [0.38] | [0.47] | [2,700] |

In Table 2, (A)-1 and (A)-A are the same as defined above, and the other reference characters indicate the following. Further, the values in brackets [ ] indicate the amount (in terms of parts by weight) of the component added.

(A)-2: a polymeric compound (A)-2 shown below
(A)-3: a polymeric compound (A)-3 shown below
(A)-4: a polymeric compound (A)-4 shown below
(A)-5: a polymeric compound (A)-5 shown below
(A)-B: a polymeric compound (A)-B shown below
(A)-C: a polymeric compound (A)-C shown below
(A)-D: a polymeric compound (A)-D shown below
(A)-E: a polymeric compound (A)-E shown below
(A)-F: a polymeric compound (A)-F shown below
(A)-G: a polymeric compound (A)-G shown below
(B)-1: a compound (B)-1 shown below
(B)-2: a compound (B)-2 shown below
(D)-1: tri-n-pentylamine
(E)-1: salicylic acid
(S)-1: a mixed solvent of PGMEA/PGME = 60/40 (weight ratio)

[Chemical Formula 63]

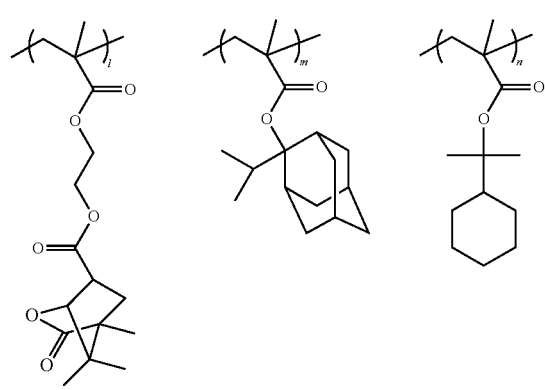

(A)-2

[Mw = 6,600, Mw/Mn = 1.57, l/m/n (molar ratio) = 36.5/12.0/51.5]

[Chemical Formula 64]

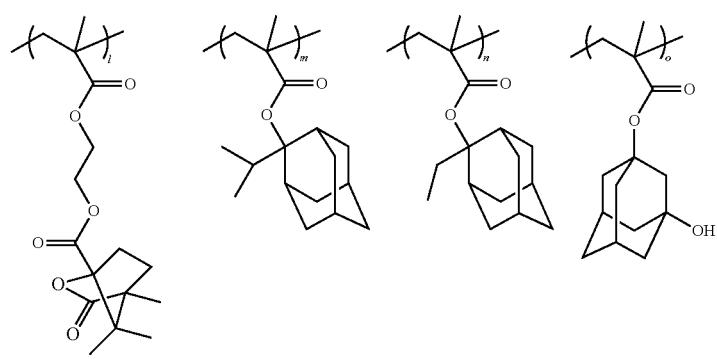

(A)-3

[Mw = 5,800, Mw/Mn = 1.63, l/m/n/o (molar ratio) = 38.3/37.5/14.5/9.7]

TABLE 2-continued
| Component (A) | Component (B) | Component (D) | Component (E) | Component (S) |
[Chemical Formula 65]
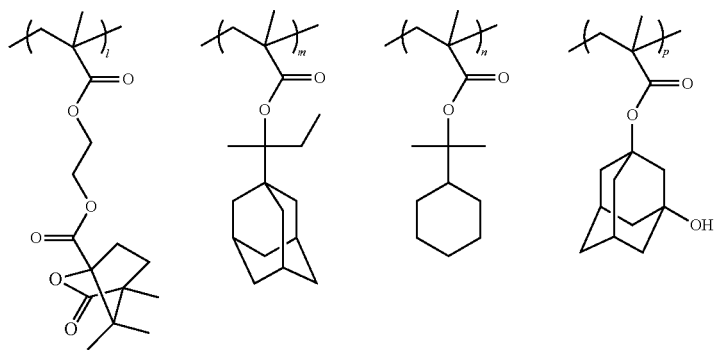
(A)-4
[Mw = 8,100, Mw/Mn = 1.65, l/m/n/p (molar ratio) = 37.6/47.9/6.3/8.2]
[Chemical Formula 66]
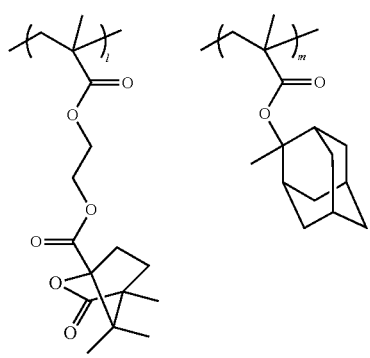
(A)-5
[Mw = 6,500, Mw/Mn = 1.69, l/m (molar ratio) = 51.2/48.8]
[Chemical Formula 67]
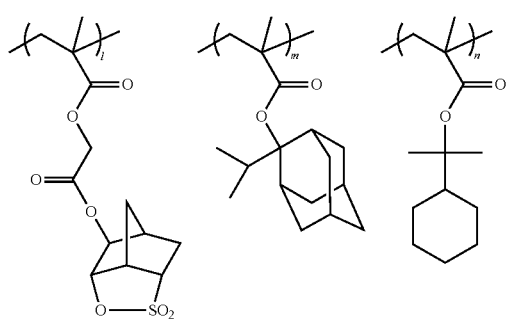
(A)-B
[Mw = 6,100, Mw/Mn = 1.61, l/m/n (molar ratio) = 40.0/10.8/49.2]

TABLE 2-continued
| Component (A) | Component (B) | Component (D) | Component (E) | Component (S) |
| --- | --- | --- | --- | --- |
[Chemical Formula 68]
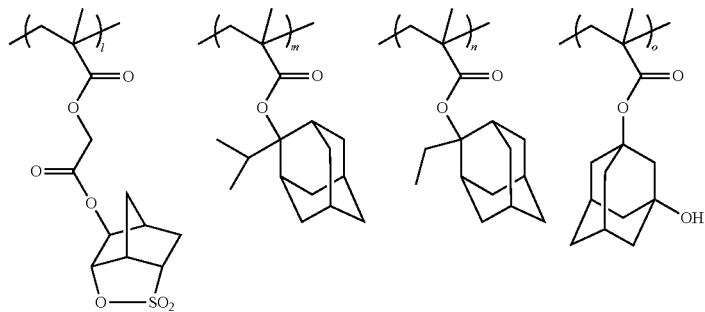
(A)-C
[Mw = 6,400, Mw/Mn = 1.55, l/m/n/o (molar ratio) = 38.5/37.9/14.6/9.0]
[Chemical Formula 69]
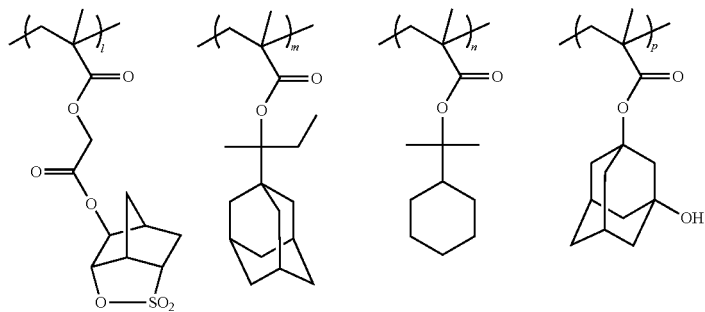
(A)-D
[Mw = 8,400, Mw/Mn = 1.59, l/m/n/p (molar ratio) = 40.2/46.6/6.7/6.5]
[Chemical Formula 70]
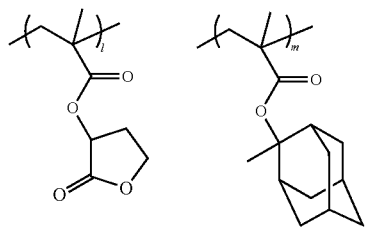
(A)-E
[Mw = 6,800, Mw/Mn = 1.92, l/m (molar ratio) = 51.2/48.8]
[Chemical Formula 71]
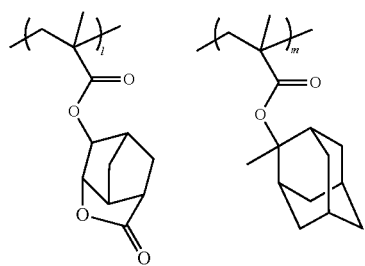
(A)-F
[Mw = 6,900, Mw/Mn = 1.98, l/m (molar ratio) = 50.8/49.2]

TABLE 2-continued

| Component (A) | Component (B) | Component (D) | Component (E) | Component (S) |

[Chemical Formula 72]

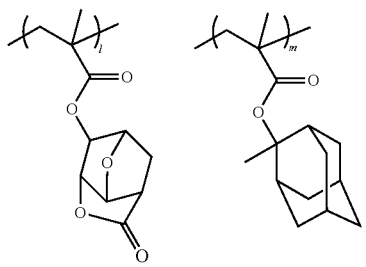

(A)-G
[Mw = 7,100, Mw/Mn = 1.88, l/m (molar ratio)= 52.1/47.9]

[Chemical Formula 73]

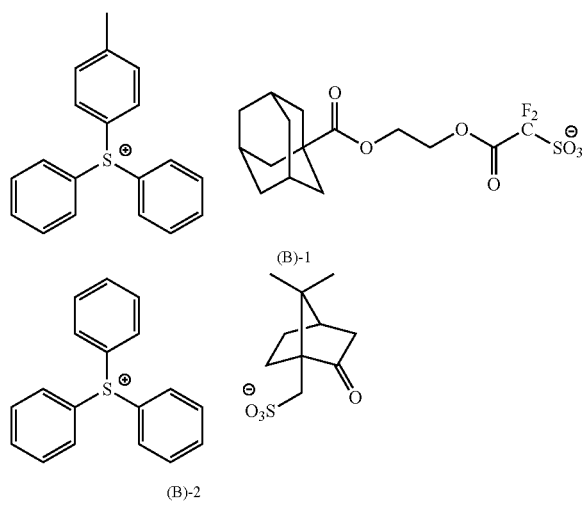

(B)-1

(B)-2

Using the obtained positive resist compositions, resist patterns were formed in accordance with the procedures below, and the following evaluations were carried out.

[Formation of Resist Pattern]

An organic antireflection film composition (product name: ARC29A, manufactured by Brewer Science Ltd.) was applied onto an 8-inch silicon wafer using a spinner, and the composition was then baked on a hotplate at 205° C. for 60 seconds, thereby forming an organic antireflection film having a film thickness of 77 nm. Then, the above resist composition was applied onto the antireflection film using a spinner, and was then prebaked (PAB) on a hotplate at the temperature indicated in Table 3 for 60 seconds and dried, thereby forming a resist film having a film thickness of 120 nm.

Subsequently, the resist film was selectively irradiated with an ArF excimer laser (193 nm) through a mask pattern (6% half tone), using an ArF exposure apparatus NSR-S302 (manufactured by Nikon Corporation; NA (numerical aperture)=0.60, ⅔ annular illumination). Thereafter, a post exposure bake (PEB) treatment was conducted at the temperature indicated in Table 3 for 60 seconds, followed by development for 30 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist film was washed for 30 seconds with pure water, followed by drying by shaking, and a postbake treatment at 100° C. for 60 seconds.

As a result, in each of the examples, a line and space (1:1) resist pattern (LS pattern) having a line width of 130 nm and a pitch of 260 nm was formed on the resist film. Further, the optimum exposure dose Eop (mJ/cm$^2$) at this time, namely the sensitivity, was determined. The results are shown in Table 3.

[Evaluation of Line Width Roughness (LWR)]

With respect to each of the LS patterns having a line width of 130 nm and a pitch of 260 nm that was formed with the above Eop, the space width at 400 points in the lengthwise direction of the space were measured using a measuring scanning electron microscope (SEM) (product name: S-9220, manufactured by Hitachi, Ltd.; acceleration voltage: 800V). From the results, the value of 3 times the standard deviation s (i.e., 3 s) was determined, and the average of the 3 s values at 400 points was calculated as a yardstick of LWR. The results are shown in Table 3.

The smaller this 3 s value is, the lower the level of roughness of the line width, indicating that a LS pattern with a uniform width was obtained.

[Resolution]

The critical resolution (nm) at the above Eop value was determined using a scanning electron microscope S-9220 (manufactured by Hitachi, Ltd.). The obtained results are indicated as "Resolution (nm)" in Table 3.

TABLE 3

| | PAB (° C.) | PEB (° C.) | Eop (mJ/cm²) | LWR (nm) | Resolution (nm) |
|---|---|---|---|---|---|
| Ex. 2 | 105 | 95 | 19.1 | 7.58 | 41.1 |
| Comp. Ex. 2 | 105 | 95 | 22.2 | 9.04 | 50.4 |
| Ex. 3 | 80 | 80 | 25.4 | 6.93 | 74.9 |
| Comp. Ex. 3 | 80 | 80 | 27.1 | 8.49 | 85.3 |
| Ex. 4 | 80 | 80 | 28.3 | 7.41 | 57.5 |
| Comp. Ex. 4 | 80 | 80 | 29.8 | 8.93 | 66.2 |
| Ex. 5 | 80 | 80 | 27.9 | 7.27 | 56.8 |
| Comp. Ex. 5 | 80 | 80 | 29.5 | 8.75 | 65.3 |
| Ex. 6 | 90 | 90 | 23.8 | 8.31 | 82.7 |
| Comp. Ex. 6 | 90 | 90 | 24.4 | 9.83 | 91.0 |
| Comp. Ex. 7 | 90 | 90 | 26.3 | 8.99 | 87.0 |
| Comp. Ex. 8 | 90 | 90 | 25.4 | 9.02 | 90.5 |

As seen from the results shown in Table 3, it was confirmed that the resist compositions of Examples 2 to 6 exhibited superior lithography properties in terms of LWR, resolution and the like, as compared to the resist compositions of Comparative Examples 2 to 8.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A resist composition comprising:
a base component (A) that exhibits changed solubility in a developing solution under action of acid; and
an acid generator component (B) that generates acid upon exposure,
wherein said base component (A) contains a resin component (A0) including a structural unit (a0) represented by general formula (a0) shown below:

[Chemical Formula 1]

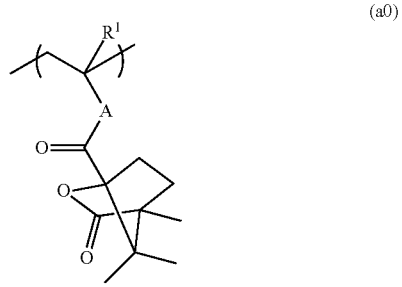

(a0)

wherein A represents a divalent linking group; and R¹ represents a hydrogen atom or a hydrocarbon group of 1 to 6 carbon atoms which may have a substituent.

2. The resist composition according to claim 1, wherein said resin component (A0) is a resin component (A1) that exhibits increased polarity under action of acid.

3. The resist composition according to claim 2, wherein said resin component (A1) includes a structural unit (a1) containing an acid decomposable group that exhibits increased polarity under action of acid.

4. The resist composition according to claim 3, wherein said resin component (A1) further includes a structural unit containing a lactone-containing cyclic group and derived from an acrylate ester in which a hydrogen atom bonded to a carbon atom on the α-position may be substituted with a substituent.

5. The resist composition according to claim 3, wherein said resin component (A1) further includes a structural unit (a3) containing a polar group-containing aliphatic hydrocarbon group and derived from an acrylate ester in which a hydrogen atom bonded to a carbon atom on the α-position may be substituted with a substituent.

6. The resist composition according to claim 1, further comprising a nitrogen-containing organic compound (D).

7. A method of forming a resist pattern, comprising:
applying the resist composition of claim 1 to a substrate to form a resist film on the substrate;
conducting exposure of said resist film; and
developing said resist film to form a resist pattern.

8. A polymeric compound comprising a structural unit (a0) represented by general formula (a0) shown below:

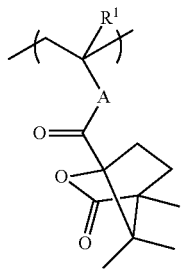

(a0)

wherein A represents a divalent linking group; and R¹ represents a hydrogen atom or a hydrocarbon group of 1 to 6 carbon atoms which may have a substituent.

9. The polymeric compound according to claim 8, which exhibits increased polarity under action of acid.

10. The polymeric compound according to claim 9, further comprising a structural unit (a1) containing an acid decomposable group that exhibits increased polarity under action of acid.

11. The polymeric compound according to claim 10, further comprising a structural unit containing a lactone-containing cyclic group and derived from an acrylate ester in which a hydrogen atom bonded to a carbon atom on the α-position may be substituted with a substituent.

12. The polymeric compound according to claim 10, further comprising a structural unit (a3) containing a polar group-containing aliphatic hydrocarbon group and derived from an acrylate ester in which a hydrogen atom bonded to a carbon atom on the α-position may be substituted with a substituent.

13. A compound represented by general formula (I) shown below:

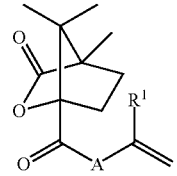

(I)

wherein A represents —O—, —C(=O)—, —C(=O)—O—, —NH—, provided that H may be replaced with a substituent, —NH—C(=O)—, =N—, —S—, —S(=O)₂—, or —S(=O)₂—O—, a combination thereof with a divalent hydrocarbon group, or a combination of —O—C(=O)—O— with a divalent hydrocarbon group; and $R^1$ represents a hydrogen atom or a hydrocarbon group of 1 to 6 carbon atoms which may have a substituent.

14. A compound represented by general formula (I) shown below:

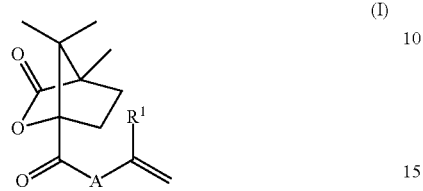

wherein A represents —C(=O)—$X^0$-$A^0$-$X^0$—, —C(=O)—$X^0$—$B^0$—$X^0$—, —$B^0$—$X^0$—, —$B^0$—C(=O)—$X^0$-$A^0$-$X^0$— or —C(=O)—$X^0$-$A^0$-$X^0$-$A^0$-$X^0$-, provided that each $X^0$ independently represents O, $NR^{04}$, S or $SO_2$—O—, provided that $R^{04}$ represents a hydrogen atom or a hydrocarbon group which may have a substituent, each $A^0$ independently represents an aliphatic hydrocarbon group which may have a substituent, each $B^0$ independently represents an aromatic hydrocarbon group, wherein a plurality of $X^0$ or $A^0$ may be the same or different, respectively; and represents a hydrogen atom or a hydrocarbon group of 1 to 6 carbon atoms which may have a substituent.

* * * * *

UNITED STATES PATENT AND TRADEMARK OFFICE
CERTIFICATE OF CORRECTION

| | | |
|---|---|---|
| PATENT NO. | : 8,609,320 B2 | Page 1 of 1 |
| APPLICATION NO. | : 13/305545 | |
| DATED | : December 17, 2013 | |
| INVENTOR(S) | : Yoshiyuki Utsumi et al. | |

It is certified that error appears in the above-identified patent and that said Letters Patent is hereby corrected as shown below:

In the Specification:

In Column 55, Line 12, Change "SO2" to --$SO_2$--.

In Column 101, Line 4, Change "R31," to --$R^{31}$,--.

In the Claims:

In Column 125, Line 28, In Claim 14, change "and" to --and $R^1$--.

Signed and Sealed this
Eighth Day of July, 2014

Michelle K. Lee
*Deputy Director of the United States Patent and Trademark Office*